US011373513B2

(12) United States Patent
Musumano

(10) Patent No.: US 11,373,513 B2
(45) Date of Patent: Jun. 28, 2022

(54) SYSTEM AND METHOD OF MANAGING PERSONAL SECURITY

(71) Applicant: Gregory Musumano, Naples, FL (US)

(72) Inventor: Gregory Musumano, Naples, FL (US)

( * ) Notice: Subject to any disclaimer, the term of this patent is extended or adjusted under 35 U.S.C. 154(b) by 0 days.

(21) Appl. No.: 16/236,325

(22) Filed: Dec. 28, 2018

(65) Prior Publication Data
US 2019/0206230 A1 Jul. 4, 2019

Related U.S. Application Data

(60) Provisional application No. 62/611,070, filed on Dec. 28, 2017.

(51) Int. Cl.
| G08B 25/01 | (2006.01) |
| H04W 4/90 | (2018.01) |
| H04M 3/42 | (2006.01) |
| G10L 25/66 | (2013.01) |
| G06F 3/01 | (2006.01) |
| G06F 3/16 | (2006.01) |
| H04L 67/00 | (2022.01) |

(52) U.S. Cl.
CPC .......... *G08B 25/016* (2013.01); *G06F 3/017* (2013.01); *G06F 3/16* (2013.01); *G10L 25/66* (2013.01); *H04L 67/00* (2013.01); *H04M 3/4217* (2013.01); *H04M 3/42229* (2013.01); *H04W 4/90* (2018.02); *H04M 2203/256* (2013.01); *H04M 2203/557* (2013.01); *H04M 2242/04* (2013.01)

(58) Field of Classification Search
None
See application file for complete search history.

(56) References Cited

U.S. PATENT DOCUMENTS

| 6,147,611 | A  | * | 11/2000 | Otero ..................... G08B 5/002 340/573.1 |
| 7,477,143 | B2 | * | 1/2009 | Albert .................... G08B 17/00 340/4.14 |
| 8,013,734 | B2 | * | 9/2011 | Saigh ................ H04M 1/72424 340/539.13 |
| 8,249,547 | B1 | * | 8/2012 | Fellner ................... H04B 1/385 455/404.1 |
| 8,424,350 | B2 | * | 4/2013 | Bernatchez ............. F41B 15/08 70/456 R |
| 8,538,374 | B1 | * | 9/2013 | Haimo .................. G01S 5/0027 455/404.2 |

(Continued)

FOREIGN PATENT DOCUMENTS

WO    WO2016116814    7/2016

*Primary Examiner* — Chico A Foxx

(57) ABSTRACT

A method of managing personal security allows a portable computing device to provide a user with a variety of automated security detection and responses. The portable computing device uses integrated hardware to assess an emergency situation from spoken distress cues, audible danger cues, medical distress cues, physical trauma cues, and manually-inputted cues. The portable computing device also provides the user with a variety of responses to the emergency situation, which include a contacting-help response, a supplemental-help response, a communal-help response, an immediate alarm response, a delayed alarm response, an informing response, an increasing-visibility response, and a decreasing-visibility response.

17 Claims, 22 Drawing Sheets

(56) References Cited

U.S. PATENT DOCUMENTS

| | | | | |
|---|---|---|---|---|
| 8,618,930 B2* | 12/2013 | Papadopoulos | A61B 5/02427 | 340/539.12 |
| 8,776,149 B1* | 7/2014 | Koch | H04N 21/44222 | 725/88 |
| 8,866,606 B1* | 10/2014 | Will | G08B 25/016 | 340/539.11 |
| 9,503,873 B1* | 11/2016 | Yadav | G01C 21/20 | |
| 9,697,720 B1* | 7/2017 | Lassiter | H04W 4/90 | |
| 9,715,819 B1* | 7/2017 | Stockdale | G08B 15/004 | |
| 9,717,101 B1* | 7/2017 | Burnham | H04W 76/50 | |
| 9,913,089 B2* | 3/2018 | Guo | H04W 4/023 | |
| 9,953,507 B1* | 4/2018 | Smith | G08B 21/043 | |
| 10,249,166 B1* | 4/2019 | Carter | G08B 6/00 | |
| 10,607,193 B1* | 3/2020 | Wender | G06Q 10/1095 | |
| 10,609,541 B1* | 3/2020 | Govindassamy | H04W 76/50 | |
| 10,778,459 B2* | 9/2020 | Keil | H04L 67/20 | |
| 10,841,780 B1* | 11/2020 | Ogaz | H04W 4/022 | |
| 2002/0069885 A1* | 6/2002 | Boies | A61B 5/0031 | 128/899 |
| 2005/0083195 A1 | 4/2005 | Pham | | |
| 2008/0291667 A1* | 11/2008 | Bushee | A62B 3/005 | 362/206 |
| 2009/0153323 A1* | 6/2009 | Nielsen | G04G 13/021 | 340/540 |
| 2010/0099461 A1* | 4/2010 | Rahfaldt | H04M 1/72541 | 455/557 |
| 2010/0103779 A1* | 4/2010 | Kakirde | G06Q 10/109 | 368/10 |
| 2010/0127878 A1* | 5/2010 | Wang | G10L 17/26 | 340/573.1 |
| 2010/0283609 A1* | 11/2010 | Remer | G08B 25/016 | 340/541 |
| 2011/0068917 A1* | 3/2011 | Puana | G08B 25/12 | 340/540 |
| 2011/0217946 A1* | 9/2011 | DeAngeles | G08B 3/10 | 455/347 |
| 2011/0298613 A1* | 12/2011 | Ben Ayed | A61B 5/7415 | 340/539.11 |
| 2012/0088466 A1* | 4/2012 | Conroy | G16H 10/60 | 455/404.1 |
| 2012/0112667 A1* | 5/2012 | Mohan | H05B 37/0218 | 315/307 |
| 2012/0225635 A1* | 9/2012 | Esbensen | H04W 4/029 | 455/404.2 |
| 2012/0319848 A1* | 12/2012 | Coffeng | A61M 16/021 | 340/573.1 |
| 2013/0005294 A1* | 1/2013 | Levinson | H04N 7/18 | 455/404.2 |
| 2013/0082837 A1* | 4/2013 | Cosentino | A61B 5/002 | 340/539.12 |
| 2013/0115972 A1* | 5/2013 | Ziskind | H04W 4/21 | 455/456.2 |
| 2013/0216065 A1* | 8/2013 | Nguyen | G08B 21/043 | 381/94.1 |
| 2013/0271277 A1* | 10/2013 | McCauley | G08B 7/06 | 340/517 |
| 2013/0312168 A1* | 11/2013 | Raanan | A61B 5/1117 | 2/465 |
| 2014/0031001 A1* | 1/2014 | Jacobsen | H04W 4/90 | 455/404.2 |
| 2014/0066000 A1* | 3/2014 | Butler | G08B 25/001 | 455/404.2 |
| 2014/0085445 A1* | 3/2014 | Joao | G01C 21/3679 | 348/61 |
| 2014/0146170 A1* | 5/2014 | Tofighbakhsh | G08B 25/016 | 348/143 |
| 2014/0187225 A1* | 7/2014 | Miller | H04L 12/1818 | 455/418 |
| 2014/0247124 A1 | 9/2014 | Ros | | |
| 2014/0251233 A1* | 9/2014 | Bianchi | G08B 23/00 | 119/720 |
| 2014/0253326 A1* | 9/2014 | Cho | G08B 7/066 | 340/539.13 |
| 2014/0337621 A1* | 11/2014 | Nakhimov | H04W 12/068 | 713/168 |
| 2015/0052578 A1* | 2/2015 | Yau | G08B 25/10 | 726/3 |
| 2015/0317356 A1* | 11/2015 | Deichler | G06Q 10/10 | 707/760 |
| 2016/0071399 A1 | 3/2016 | Altman et al. | | |
| 2016/0155309 A1* | 6/2016 | Watson | A61B 5/7282 | 600/324 |
| 2016/0171871 A1* | 6/2016 | Zhang | H04M 1/72463 | 340/4.31 |
| 2016/0302050 A1* | 10/2016 | Blando | H04W 4/90 | |
| 2016/0342581 A1* | 11/2016 | Delgado | G06F 3/04842 | |
| 2016/0354285 A1* | 12/2016 | Nolan | G06Q 10/109 | |
| 2016/0378325 A1* | 12/2016 | Hurley | H04W 4/029 | 715/809 |
| 2017/0186307 A1* | 6/2017 | Kim | H04N 7/188 | |
| 2017/0188216 A1* | 6/2017 | Koskas | H04W 4/90 | |
| 2017/0193308 A1* | 7/2017 | Buyse | G08B 21/0446 | |
| 2017/0345285 A1* | 11/2017 | Merjanian | H04L 67/26 | |
| 2018/0020530 A1* | 1/2018 | Scordato | H05B 37/0236 | |
| 2018/0199546 A1* | 7/2018 | Temel | A01K 27/001 | |
| 2018/0261078 A1* | 9/2018 | Meredith | H04W 4/90 | |
| 2019/0103011 A1* | 4/2019 | Ros | G08B 25/016 | |
| 2019/0147721 A1* | 5/2019 | Avitan | G08B 21/043 | 340/573.1 |
| 2021/0110682 A1* | 4/2021 | Howard | G08B 7/00 | |

* cited by examiner

SYSTEM AND METHOD OF MANAGING PERSONAL SECURITY

The current application claims a priority to the U.S. Provisional Patent application Ser. No. 62/611,070 filed on Dec. 28, 2018.

FIELD OF THE INVENTION

The present disclosure generally relates to the field of personal security. More specifically, the present disclosure relates to a platform, a system, and a device, to facilitate personal security.

BACKGROUND OF THE INVENTION

Methods to transmit emergency broadcasts have grown exponentially with advancements in communication technologies. Additionally, individuals are now able to transmit emergency broadcasts and through their smartphones and computers and even niche devices over the internet and other communication networks.

However, all present devices that facilitate personal security have to be operated manually. Further, existing devices do not facilitate individuals with a method to detect threat levels automatically from the surroundings.

Further, existing methods and devices and to facilitate threat detection are not able to detect threats to individuals from other individuals, and vicious animals. Additionally, existing devices used for emergency broadcasts do not transmit supporting data that may allow the receivers of the emergency broadcasts to have a better understanding about the gravity of the threat that the individual may be facing.

Further, present devices do not make use of sensory data to analyze the surroundings of the user constantly to detect whether a threat may be present. Further, transmission of online broadcasts is triggered by manual switches and may not be voice triggered in present devices.

Further, present devices do not analyze the health conditions of the individuals and transmit emergency broadcasts to emergency services or contacts on the individuals using the said devices.

Further, existing devices do not help the individuals in deterring threats from individuals or vicious animals while transmitting emergency broadcasts.

Further, present devices do not allow multiple individuals to contact each other at the same time in a conference to detect the level of threats or analyzing the situations so that the situations may be able to strategize and better combat any situation.

Further, existing devices do not support third party applications and devices to monitor or control the devices.

Further, existing devices do not detect the behavior of bullying or cyberbullying from external sources against individuals. Further, present devices do not collect any evidence of bullying or verbal threats from external sources made to individuals.

Further, existing devices do not detect threats from online sources in the form of viruses or malware.

Further, existing devices do not make use of crowdsourcing to help individuals deter threats with the help of other individuals.

Therefore, there is a need for improved systems and games to help improve memory retention and increasing attention span of players that may overcome one or more of the above-mentioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

According to some embodiments, the present disclosure provides an online platform configured to communicate with a personal security device to facilitate personal safety and security for users. The personal security device may allow users to contact emergency services, emergency contacts set by the user, and to set off a distress alarm in situations of emergency.

The personal security device may receive inputs from the environment of the user and may determine when a threat is present.

A threat may be defined as a possibility of pain, injury, damage, or other hostile action to the user from any source. The threat may be determined to be present by the personal security device through means such as voice recognition of keywords like "help" or other keywords.

Further, the personal security device may contain a health alert feature that may detect the heart rate, and blood pressure, of the user and may engage the emergency features of the personal security device if the personal security device detects senses an extreme rise or fall in the user's heart rate.

Further, the personal security device may also help in deterring attacks on the user by other individuals. The user may program keywords and/or voice tones to initiate the security features of the personal security device.

Further, the personal security device may also deter attacks on the user from vicious animals like stray dogs. The user may program the personal security device with the sounds and tones of aggressive animals to recognize the sounds and tones and engage the emergency features of the personal security device.

Further, the personal security device may also contain a trip timer function. The trip timer function may allow the user to set a time within which the user may have to turn the trip timer off manually.

Further, the personal security device may include fastening mechanisms so that the user may be able to fasten the personal security device to the body so that the personal security device may be more resistant to forced removal.

Further, the personal security device may also have military applications. Multiple military personnel, including soldiers, officers, and the personnel in military bases may be equipped with personal security devices. Military personnel may be constantly able to monitor an active situation from the point of view of any soldier through the corresponding personal security device.

Further, the personal security device may also include support for third-party voice recognition software, voice-controlled smart speakers like the Amazon Echo® and intelligent personal assistants like Amazon Alexa®. The personal security device may be able to connect to third-party applications like the Alexa® app and to voice-operated speakers like the Amazon Echo® or the Amazon Echo Dot®.

Further, the personal security device may also include an anti-bullying feature. The personal security device may receive inputs from sensors like microphones, and cameras, and process the received information to ascertain whether the inputs received may be considered as bullying of the user. The personal security device may also detect and help in the prevention of cyberbullying.

Further, the personal security device may also receive information like restraining orders that the user may have against other individuals, or from other individuals, parole information, and any other legal information, and may alert the concerned authorities, emergency contacts, or even the user if a restraining order or a parole order is being violated.

Further, the personal security device may also include self-defense and personal security tips and illustrations.

Further, the online platform may allow multiple users with personal security devices to build a trust circle. A trust-circle may be a collection of users who may add each other to their circle and may receive notifications about other users in the trust circle.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and subcombinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAILED DESCRIPTION OF THE INVENTION

All illustrations of the drawings are for the purpose of describing selected versions of the present invention and are not intended to limit the scope of the present invention.

Figure 1:
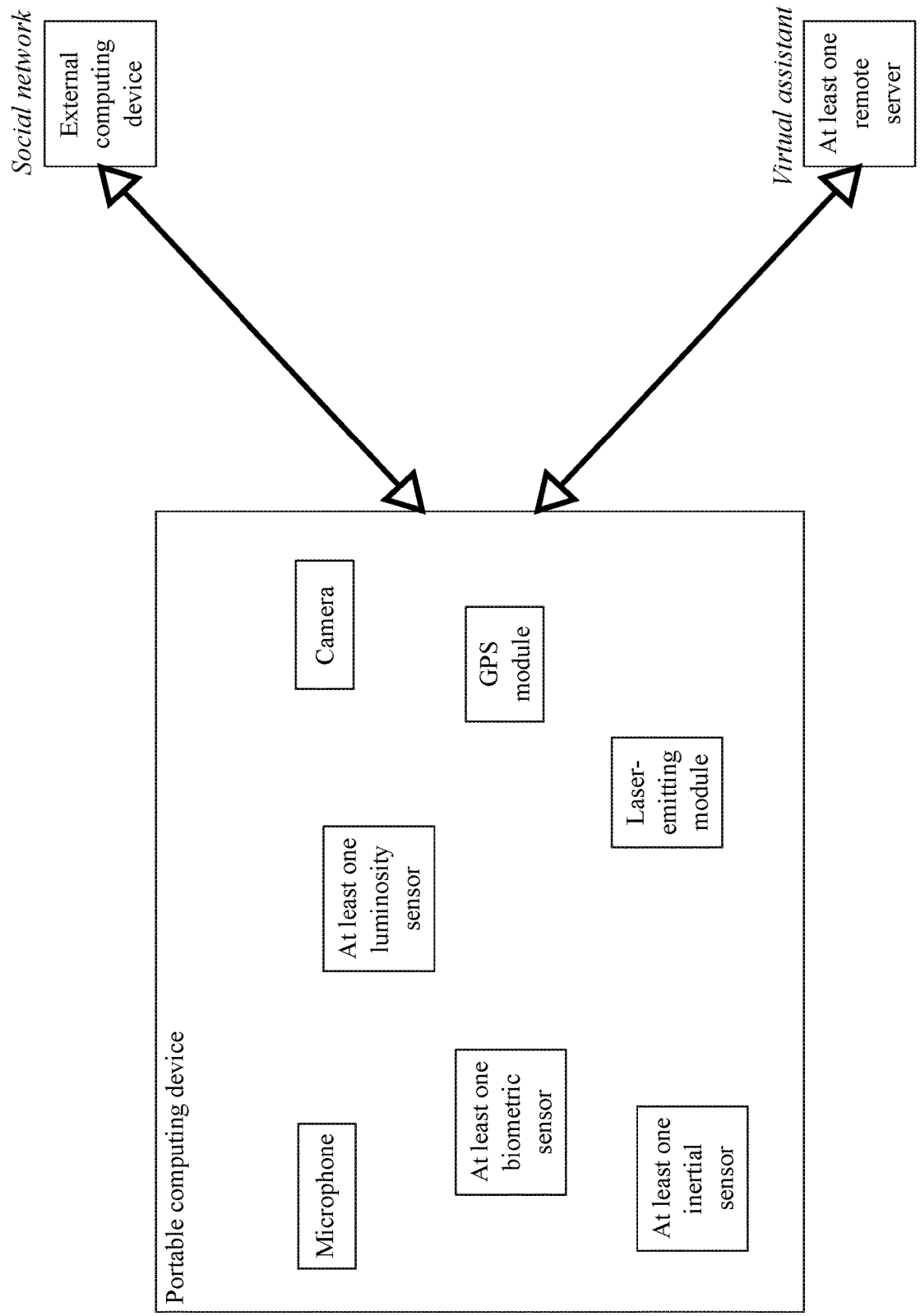
FIG. 1 is a block diagram illustrating the system of the present invention.
Figure 2:
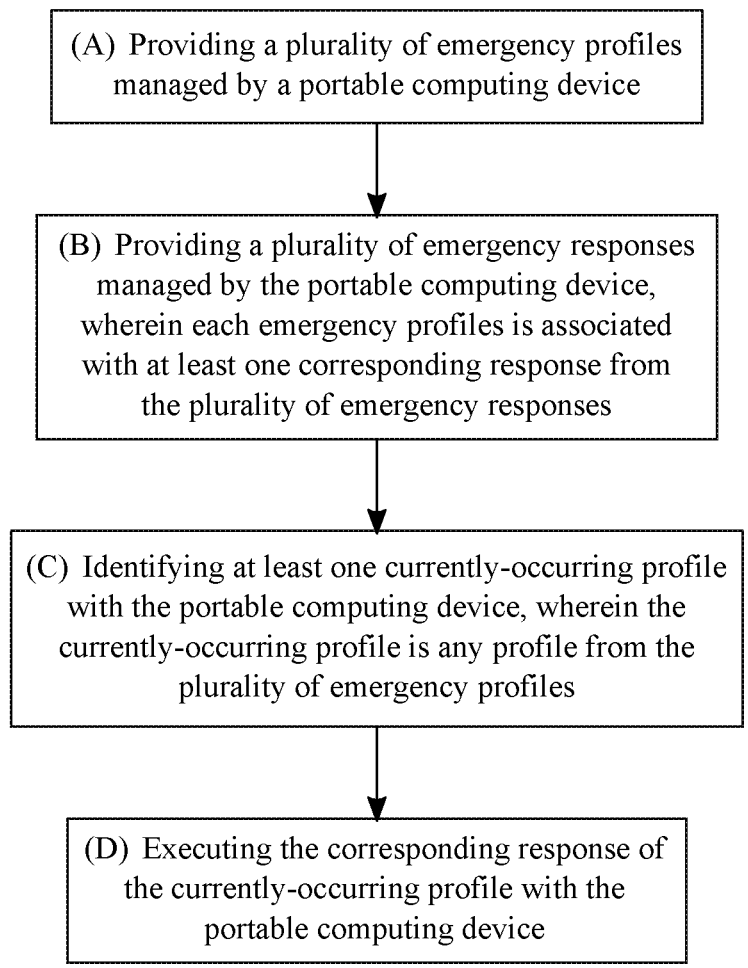
FIG. 2 is a flowchart illustrating the overall process for the method of the present invention.

The present invention is a system and a method of managing personal security by providing a user with automated features that are readily accessible through a portable computing device, which can be, but is not limited to, a smartphone, a smartwatch, a smartglasses, a laptop, and a tablet personal computer. The portable computing device may be configured into any other kind of wearable item, such as a hat, a helmet, a necklace, a wristband, etc. The present invention is used to deter or assist in situations that compromise the user's safety. Such situations include, but are not limited to, an abduction of the user, a physical attack against the user, and environmental dangers. As can be seen in FIGS. 1 and 2, the system of the present invention includes the portable computing device that is able to manage a plurality of emergency profiles (Step A) and is able to manage a plurality of emergency responses (Step B). An emergency profile is a set of predetermined conditions that need to be identified by the portable computing device so that the portable computing device is able to assess a threat to the user's safety. Each of these emergency profiles is associated with at least one corresponding response from the plurality of emergency responses. Consequently, an emergency response is a set of predetermined actions that are executed by the portable computing device in order to eliminate or reduce the threat to the user's safety. In some embodiments, the portable computing device is configured with a user restraint, such as a wrist strap, so that an attacker or an abductor cannot easily separate the portable computing device from the user.

As can be seen in FIG. 2, the method of the present invention follows an overall process in order to identify and eliminate/reduce threats to the user's safety. The overall process begins by identifying at least one currently-occurring profile with the portable computing device (Step C). The present invention allows a user to deal with different kinds of situations that threaten personal security, but the present invention needs to provide an appropriate response to a specific situation in a timely manner. Consequently, the kind of situation that is currently being assessed by the portable computing device is the currently-occurring profile, which can be any profile from the plurality of emergency profiles. The present invention also allows the portable computing device to identify multiple currently-occurring profiles at the same time. The overall process continues by executing the corresponding response of the currently-occurring profile with the portable computing device (Step D). The corresponding response of the currently-occurring profile is an automated feature of the portable computing device that is triggered by something currently threating the user's safety. In addition, the present invention allows the portable computing device to execute multiple corresponding responses for the same emergency profile.

Figure 3:
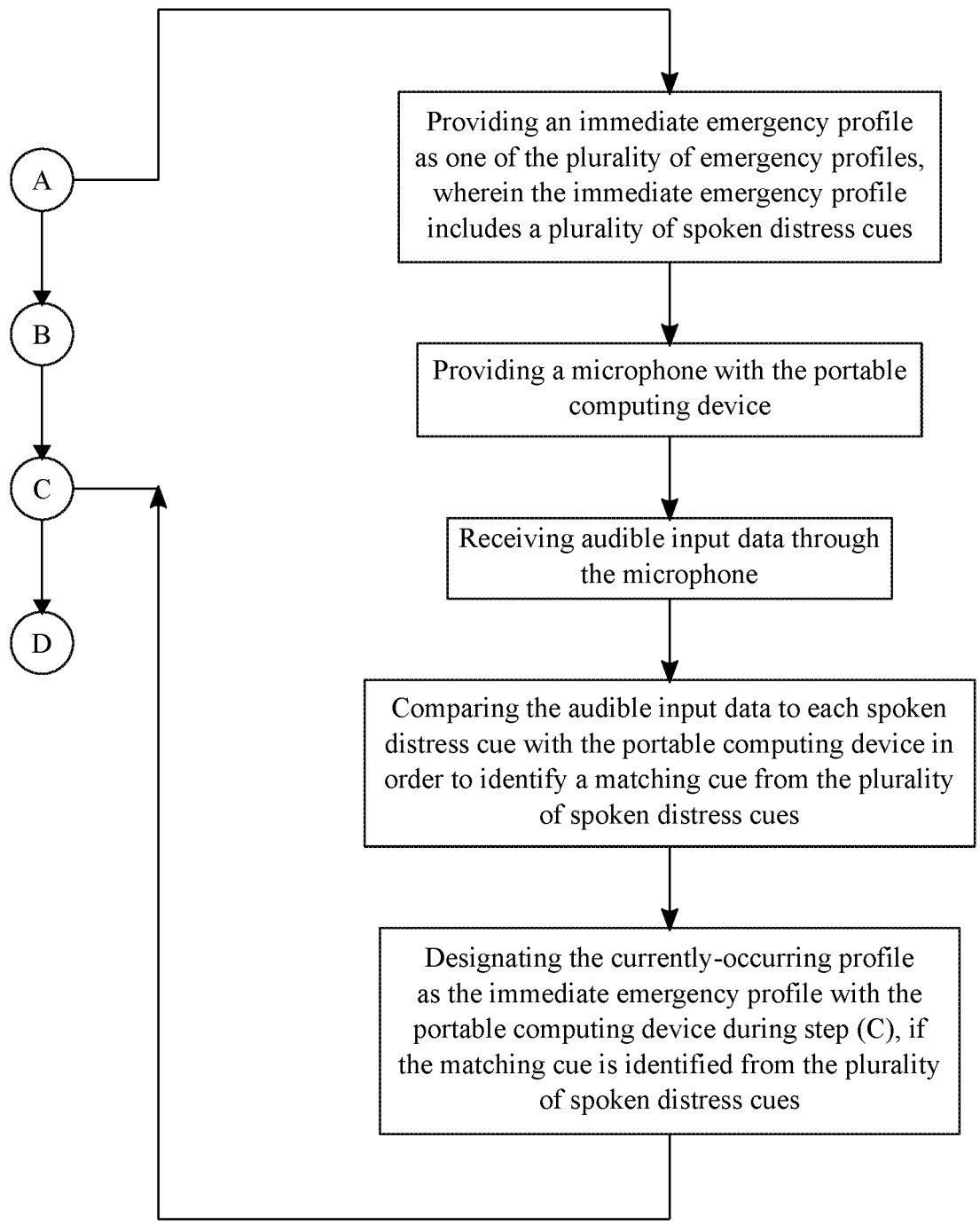
FIG. 3 is a flowchart illustrating a subprocess to automatically identify an immediate emergency with a plurality of spoken distress cues.

An immediate emergency profile is one of the plurality of emergency profiles. If the portable computing device assesses an immediate emergency profile, then the present invention is able to recognize an imminent threat to the user's safety. The method of the present invention implements different subprocesses in order to assess an immediate emergency profile. As can be seen in FIG. 3, one subprocess to assess an immediate emergency profile requires a plurality of spoken distress cues, which are typical verbal outbursts that are said by a person in imminent danger. For example, some spoken distress cues include, but are not limited to, yelling "help" and screaming "get away". The spoken distress cues are also stored on the portable computing device so that the portable computing device is able to only recognize the spoken verbal distress cues from the user, not another person. Moreover, this subprocess begins by receiving audible input data through a microphone of the portable computing device. The audible input data is the ambient sound generated near the portable computing device. This subprocess continues by comparing the audible input data to each spoken distress cue with the portable computing device in order to identify a matching cue from the plurality of spoken distress cues. The matching cue needs to be identified from the plurality of spoken distress cues so that other random words spoken by the user or other ambient noises do not trigger the portable computing device to assess an immediate emergency profile. However, if the matching cue is identified from the plurality of spoken distress cues, then the portable computing device designates the currently-occurring profile as an immediate danger profile during Step C.

Figure 4:
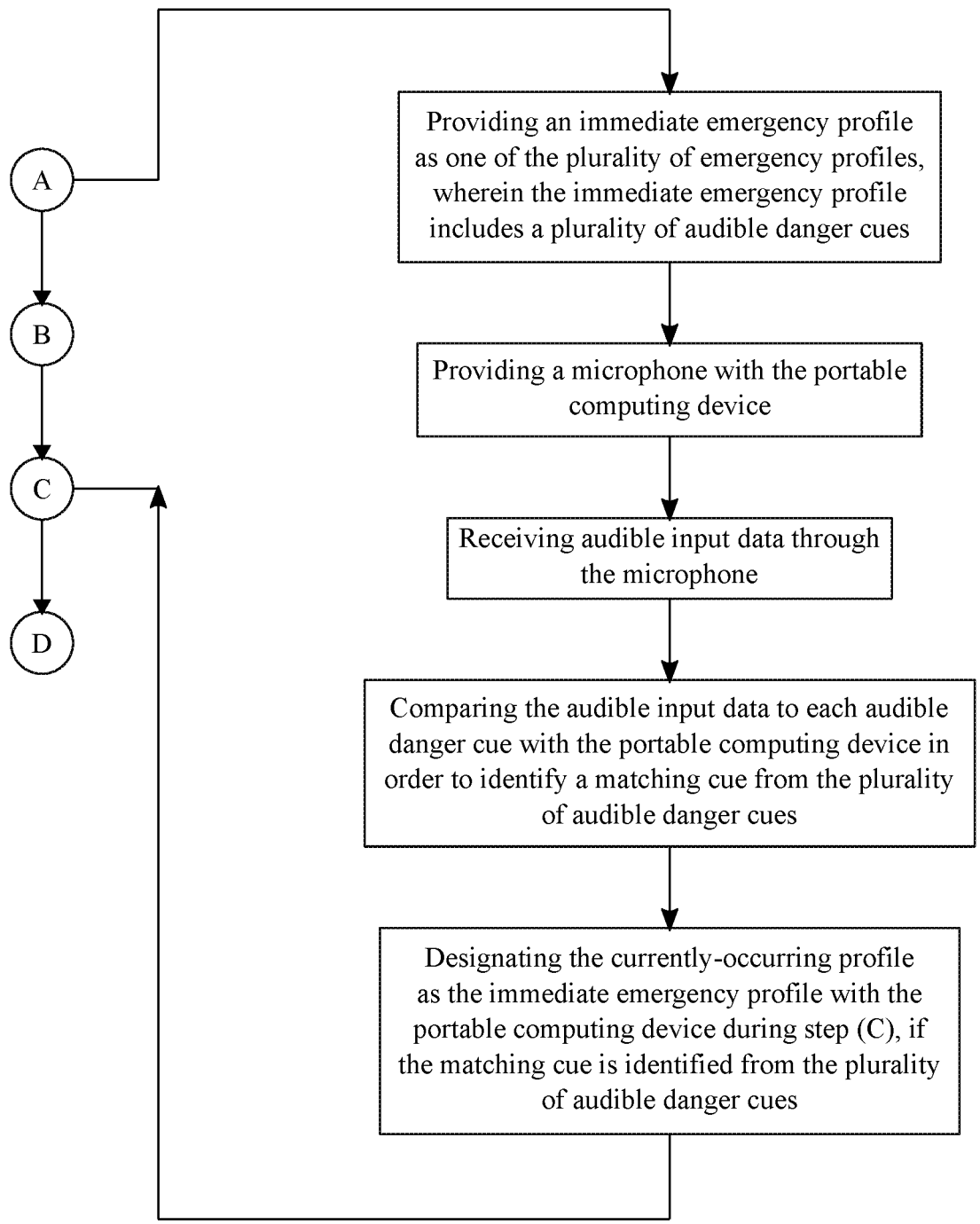
FIG. 4 is a flowchart illustrating a subprocess to automatically identify an immediate emergency with a plurality of audible danger cues.

As can be seen in FIG. 4, another similar subprocess to assess an immediate emergency profile requires a plurality of audible danger cues, which are sounds or noises that arise from dangerous situations. For example, some audible danger cues include, but are not limited to, the sound of an attacking canine or the sound of a gunshot. Moreover, this subprocess begins by receiving audible input data through the microphone of the portable computing device. Again, the audible input data is the ambient sound generated near the portable computing device. This subprocess continues by comparing the audible input data to each audible danger cue with the portable computing device in order to identify a matching cue from the plurality of spoken distress cues. Likewise, the matching cue needs to be identified from the plurality of audible danger cues so that other ambient sounds or noises do not trigger the portable computing device to assess an immediate emergency profile. However, if the matching cue is identified from the plurality of audible danger cues, then the portable computing device designates the currently-occurring profile as an immediate danger profile during Step C.

Figure 5:
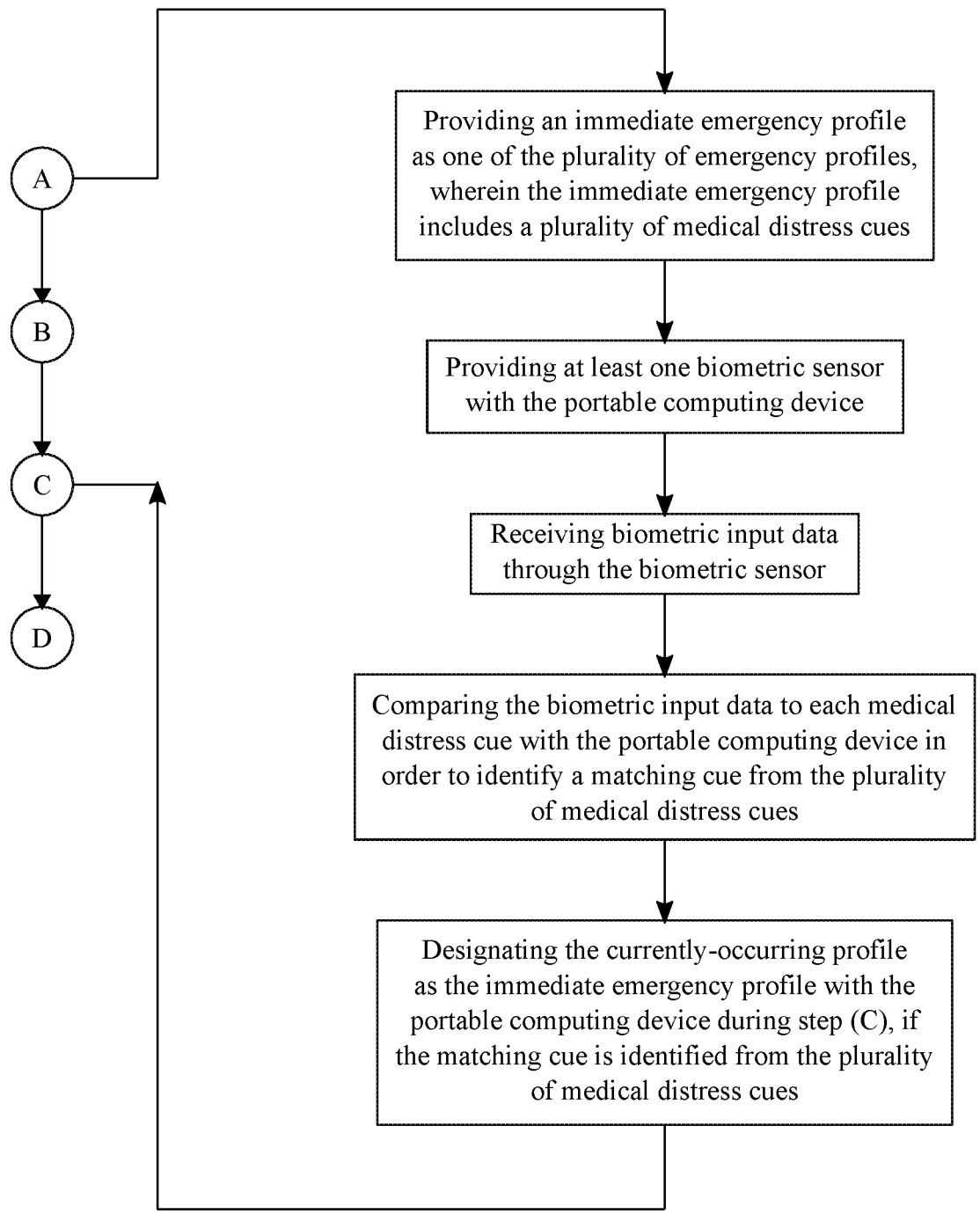
FIG. 5 is a flowchart illustrating a subprocess to automatically identify an immediate emergency with a plurality of medical distress cues.

As can be seen in FIG. 5, another similar subprocess to assess an immediate emergency profile requires a plurality of medical distress cues, which are typical physical responses by the user's body that are experienced by a person in imminent danger or by an unhealthy person. For example, some medical distress cues include, but are not limited to, an abnormal increase in heartrate, an abnormal increase in blood pressure, and an abnormal change in body temperature. Moreover, this subprocess begins by receiving biometric input data through at least one biometric sensor of the portable computing device. The biometric sensor detects changes in the physical condition of the user's body, and, consequently, the biometric input data is the current readings of the user's body that are taken by the biometric sensor. The present invention also allows the user's body to be monitored by multiple kinds of biometric sensors including, but not limited to, an electrocardiography (EKG) device and a thermometer. This subprocess continues by comparing the biometric input data to each medical distress cue with the portable computing device in order to identify a matching cue from the plurality of medical distress cues. The matching cue needs to be identified from the plurality of medical distress cues so that normal changes in the physical condition of the user's body (e.g. from exercising or sleeping) do not trigger the portable computing device to assess an immediate emergency profile. However, if the matching cue is identified from the plurality of medical distress cues, then the portable computing device designates the currently-occurring profile as an immediate danger profile during Step C.

Figure 6:
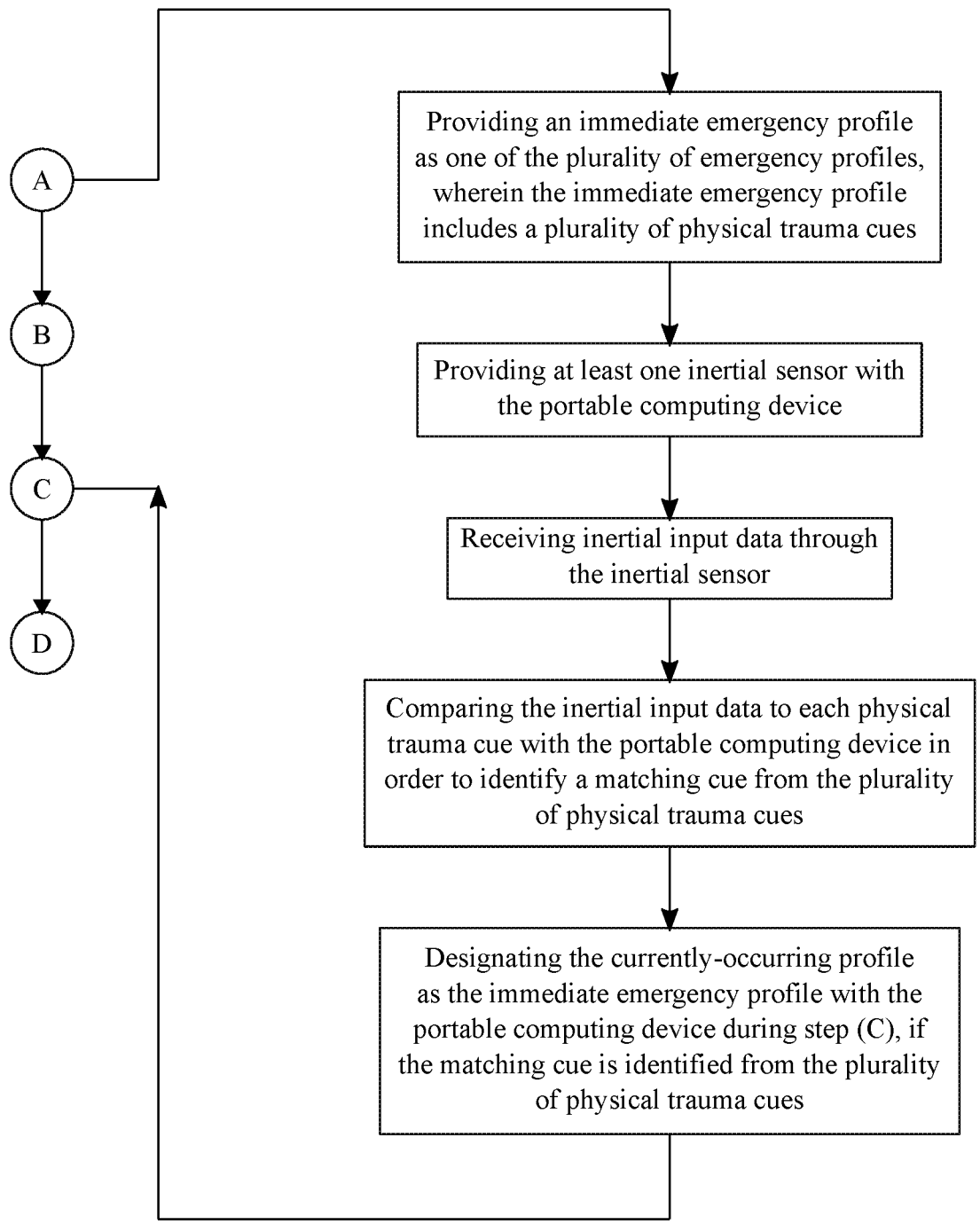
FIG. 6 is a flowchart illustrating a subprocess to automatically identify an immediate emergency with a plurality of physical trauma cues.

As can be seen in FIG. 6, another similar subprocess to assess an immediate emergency profile requires a plurality of physical trauma cues, which are external forces applied onto the user's body that are experienced by a person in imminent danger. For example, some physical trauma cues include, but are not limited to, movements from physically assaulting the user and movements against the user's will (e.g. rape or abduction). Moreover, this subprocess begins by receiving inertial input data through at least one inertial sensor of the portable computing device. The inertial sensor detects sudden movements in the user's body, and, consequently, the inertial input data is the spatial positioning and orientation readings of the user's body that are taken by the inertial sensor. The present invention also allows the user's body to be monitored by multiple kinds of inertial sensors including, but not limited to, an accelerometer, a gyroscope, and a magnetometer. This subprocess continues by comparing the inertial input data to each physical trauma cue with the portable computing device in order to identify a matching cue from the plurality of physical trauma cues. The matching cue needs to be identified from the plurality of physical trauma cues so that normal external forces applied to the user's body (e.g. driving in a car) do not trigger the portable computing device to assess an immediate emergency profile. However, if the matching cue is identified from the plurality of physical trauma cues, then the portable computing device designates the currently-occurring profile as an immediate danger profile during Step C.

Figure 7:
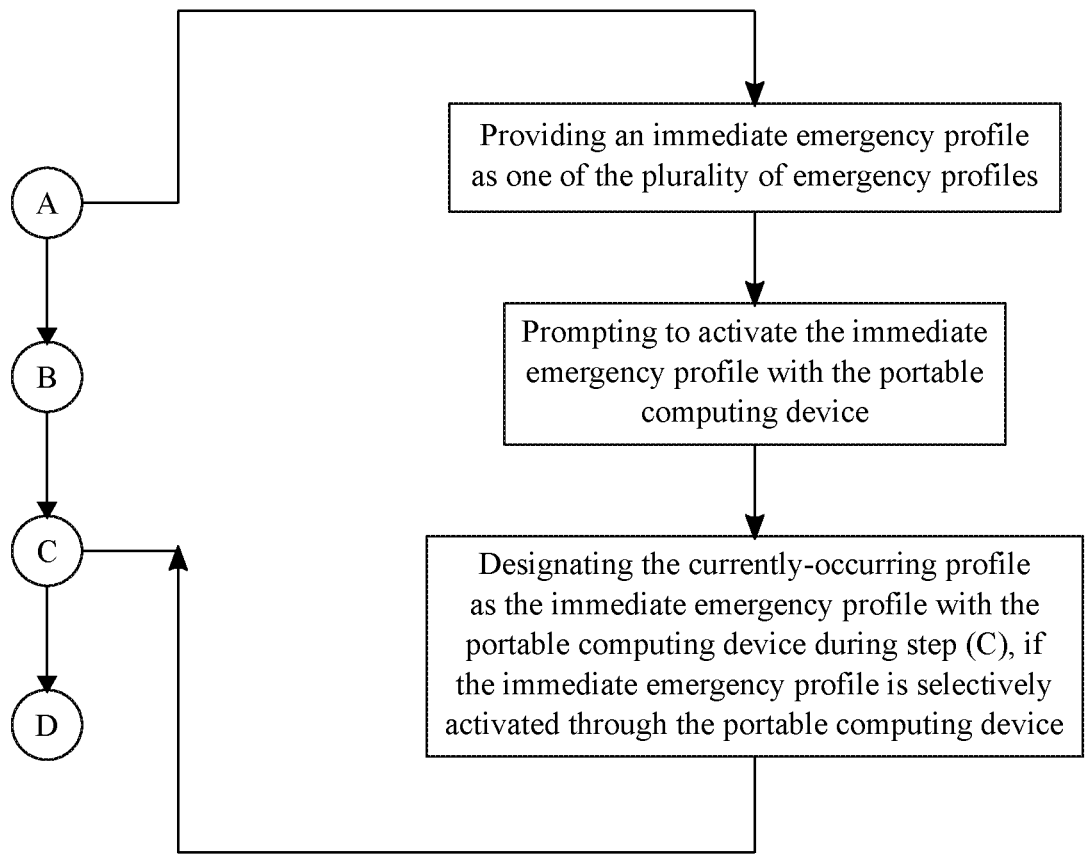
FIG. 7 is a flowchart illustrating a subprocess to manually identify an immediate emergency.

As can be seen in FIG. 7, another similar subprocess to assess an immediate emergency profile requires the user to manually activate the immediate emergency profile in case the portable computing device does not automatically assess the immediate emergency profile. For example, if the user overdoses on a drug, then the user can manually activate the immediate emergency profile through the portable computing device, before the effects of overdosing start to severely affect the user. Moreover, this subprocess begins by prompting to activate the immediate emergency profile with the portable computing device. The portable computing device can prompt the user with a virtual button on a touchscreen, a hardwired button, or any other means of entering a user input. The subprocess concludes by designating the currently-occurring profile as the immediate emergency profile with the portable computing device during Step C, if the immediate emergency profile is selectively activated through the portable computing device.

Figure 8:
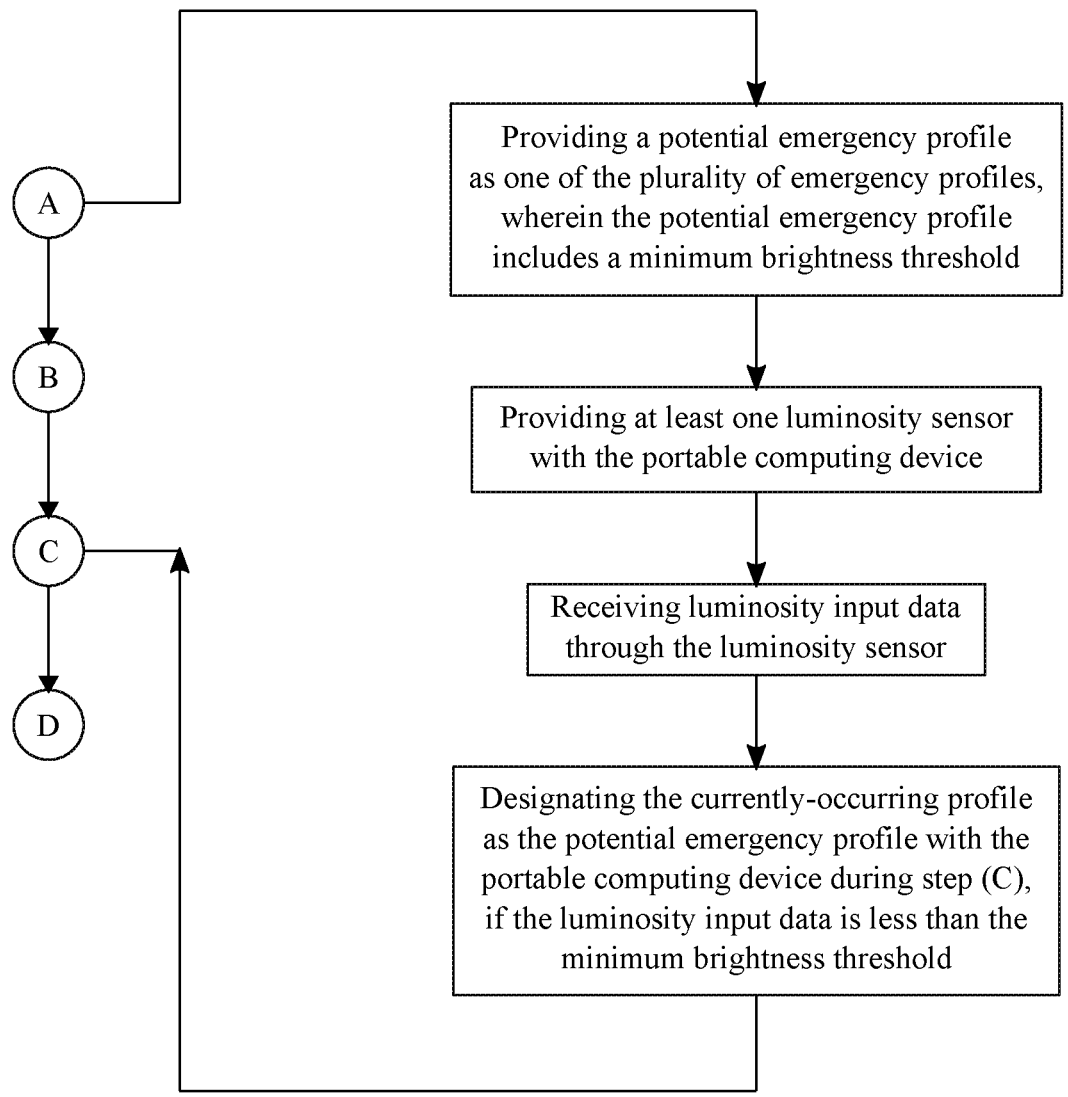
FIG. 8 is a flowchart illustrating a subprocess to automatically identify a potential emergency with a minimum brightness threshold.

A potential emergency profile is one of the plurality of emergency profiles. If the portable computing device assesses a potential emergency profile, then the present invention is able to recognize a lower-priority threat to the user's safety than the immediate emergency profile. The method of the present invention implements different subprocesses in order to assess a potential emergency profile. As can be seen in FIG. 8, one subprocess to assess a potential emergency profile requires a minimum brightness threshold, which is the brightness level that the user is not able to visually discern objects (i.e. too dark for the user to see anything). Thus, the minimum brightness threshold allows the portable computing device to recognize a potential threat to the user's safety as the user moves around in the dark. Moreover, this subprocess begins by receiving luminosity input data through at least one luminosity sensor of the portable computing device. The luminosity sensor detects the brightness level of light, and, consequently, the luminosity input data is the brightness level of the ambient light around the portable computing device. The subprocess concludes by designating the currently-occurring profile as the potential emergency profile with the portable computing device during Step C, if the luminosity input data is less than the minimum brightness threshold.

Figure 9:
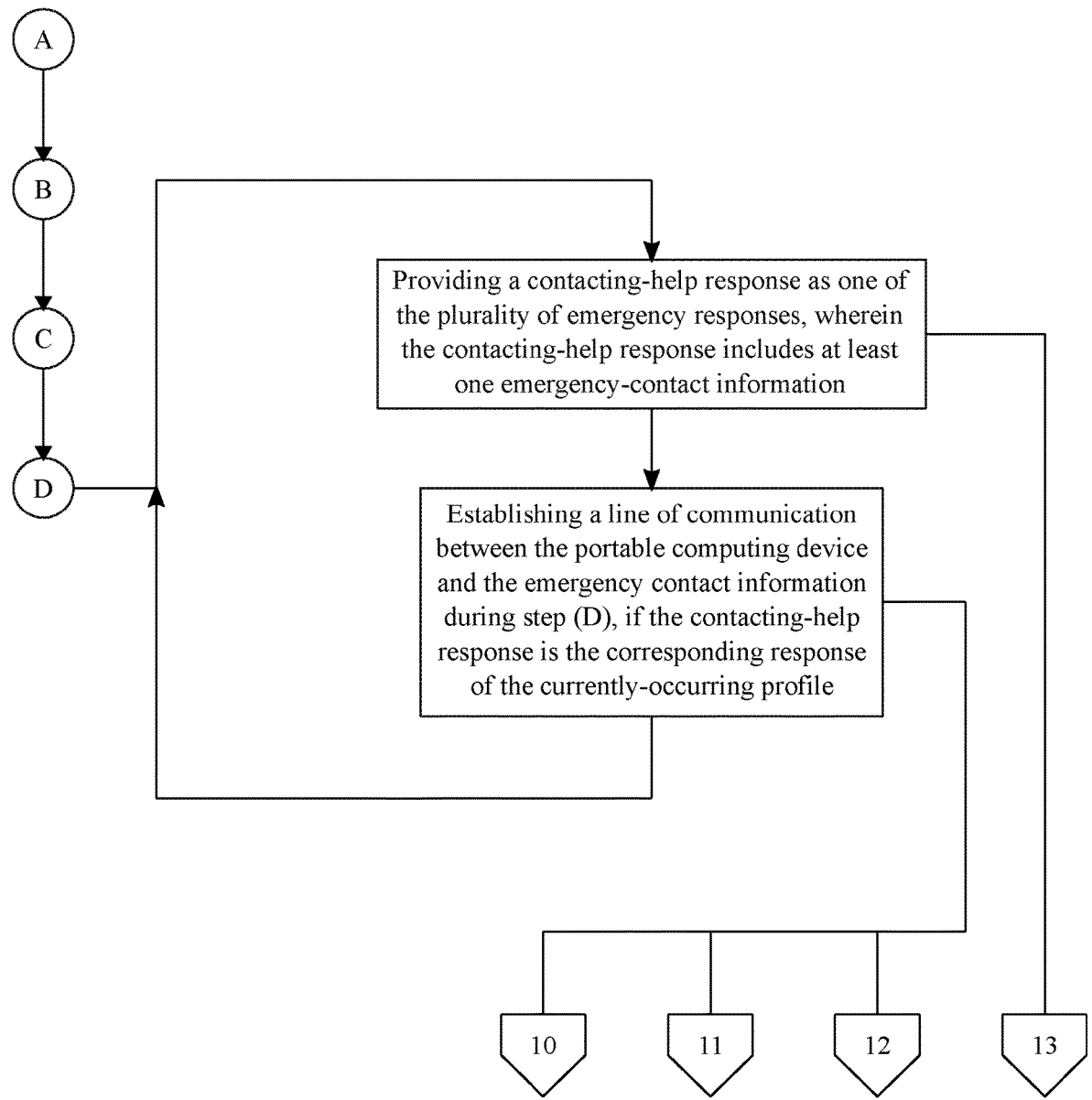
FIG. 9 is a flowchart illustrating a subprocess to execute a contacting-help response for an emergency.
Figure 13:
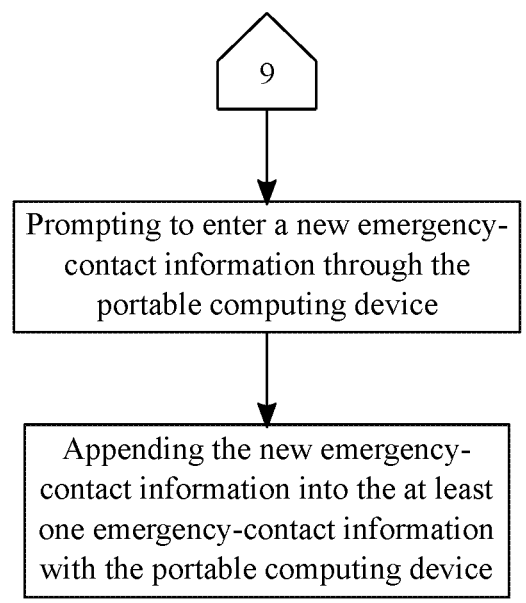
FIG. 13 is a continuation of FIG. 9 and is a flowchart illustrating a subprocess to add new emergency contacts.

The plurality of emergency responses allows the present invention in order to eliminate or reduce a threat to the user's safety. The method of the present invention implements different subprocesses in order to accommodate each kind of emergency response. As can be seen in FIG. 9, one subprocess implements a contacting-help response as one of the plurality of emergency responses, which requires at least one emergency-contact information. The contacting-help response allows the user to communicate with first responders (i.e. 911), well-trusted friends, friends that located nearby, or anyone else that can provide assistance to the user. The contacting-help response is typically a corresponding response for an immediate emergency profile, but the contacting-help response can also be a corresponding response for a potential emergency profile. Moreover, if the contacting-help response is the corresponding response of the currently-occurring profile, then a line of communication is established between the portable computing device and the emergency-contact information during Step D. In addition, the present invention allows the user to add new contacts to their list of emergency contacts because a user's list of emergency contacts changes over the course of the user's lifetime. The user could also reach out to a different emergency contact for each different kind of emergency situation. Thus, the portable computing device prompts to enter a new emergency-contact information and appends the new emergency-contact information into the existing list of emergency contacts, which is shown in FIG. 13.

Figure 10:
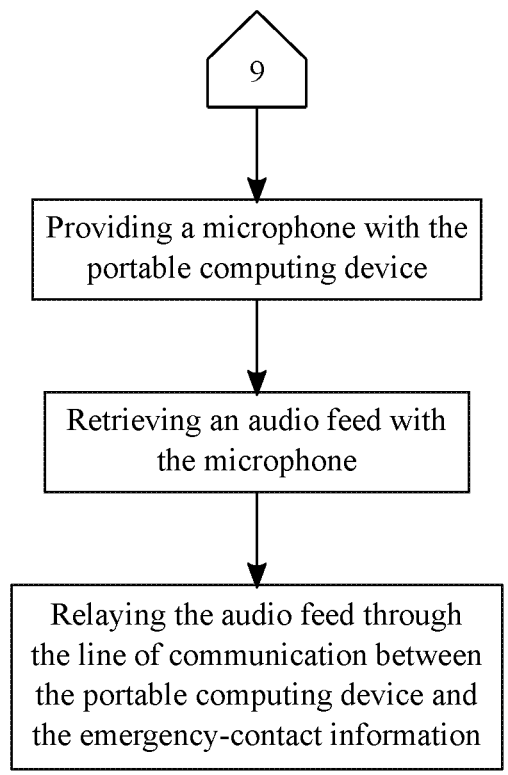
FIG. 10 is a continuation of FIG. 9 and is a flowchart illustrating a subprocess to establishing an audio feed.
Figure 11:
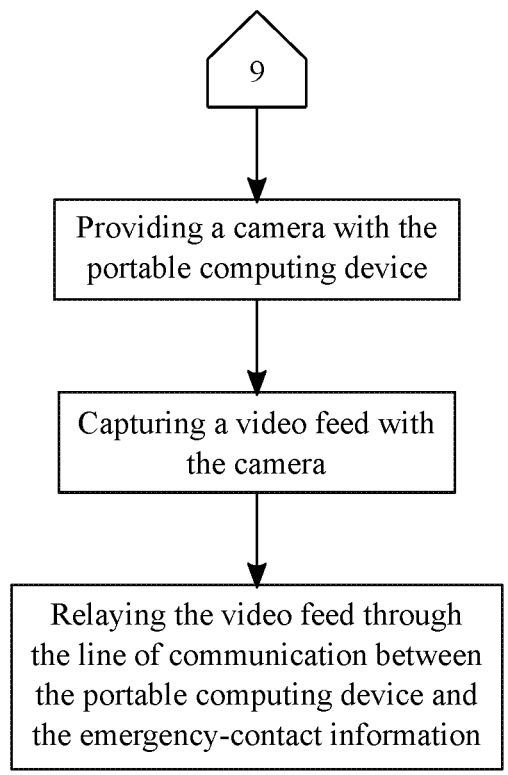
FIG. 11 is a continuation of FIG. 9 and is a flowchart illustrating a subprocess to establishing a video feed.
Figure 12:
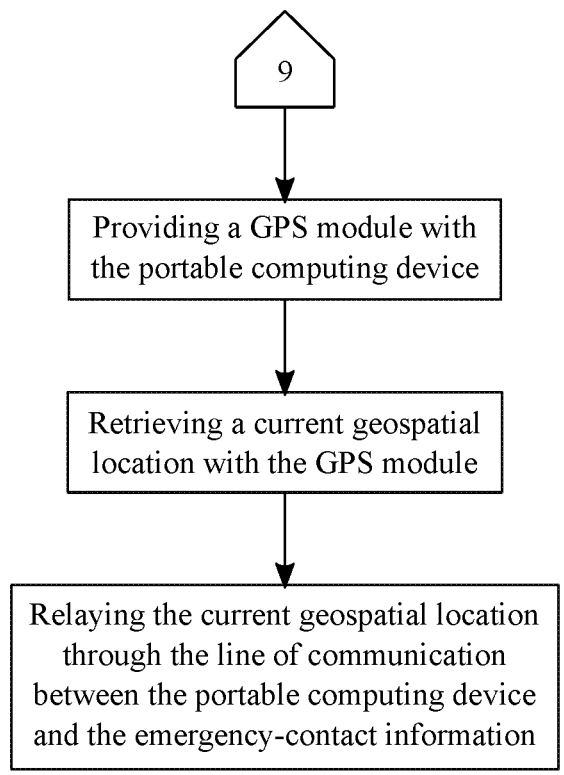
FIG. 12 is a continuation of FIG. 9 and is a flowchart illustrating a subprocess to retrieve a current geospatial location.

The contacting-help response allows different kinds of data to be transferred from the portable computing device to the emergency-contact information. As can be seen from FIG. 11, one kind of transferable data is video data, which requires the portable computing device to have a camera. The camera is used to capture a video feed, which is then relayed from the portable computing device to the emergency-contact information. For example, the video feed can be used by the emergency contact to examine the user's body during a medical emergency or to view the surroundings as the user is abducted by someone else. As can be seen in FIG. 10, another kind of transferable data is audio data, which requires the portable computing device to have a microphone. The microphone is used to capture an audio feed, which is then relayed from the portable computing device to the emergency-contact information. For example, the audio feed can be used by the emergency contact to understand the details of an emergency or to listen to sounds and noises as clues as the user is abducted by someone else. As can be seen in FIG. 12, another kind of transferable data is geospatial location data, which requires the portable computing device to have a global position system (GPS) module. The GPS module is used to retrieve the current geospatial location, which is then relayed from the portable computing device to the emergency-contact information. For example, the current geospatial location can be used by the emergency contact to know where to send the first responders or to track the whereabouts of the user as the user is abducted by someone else.

Figure 14:
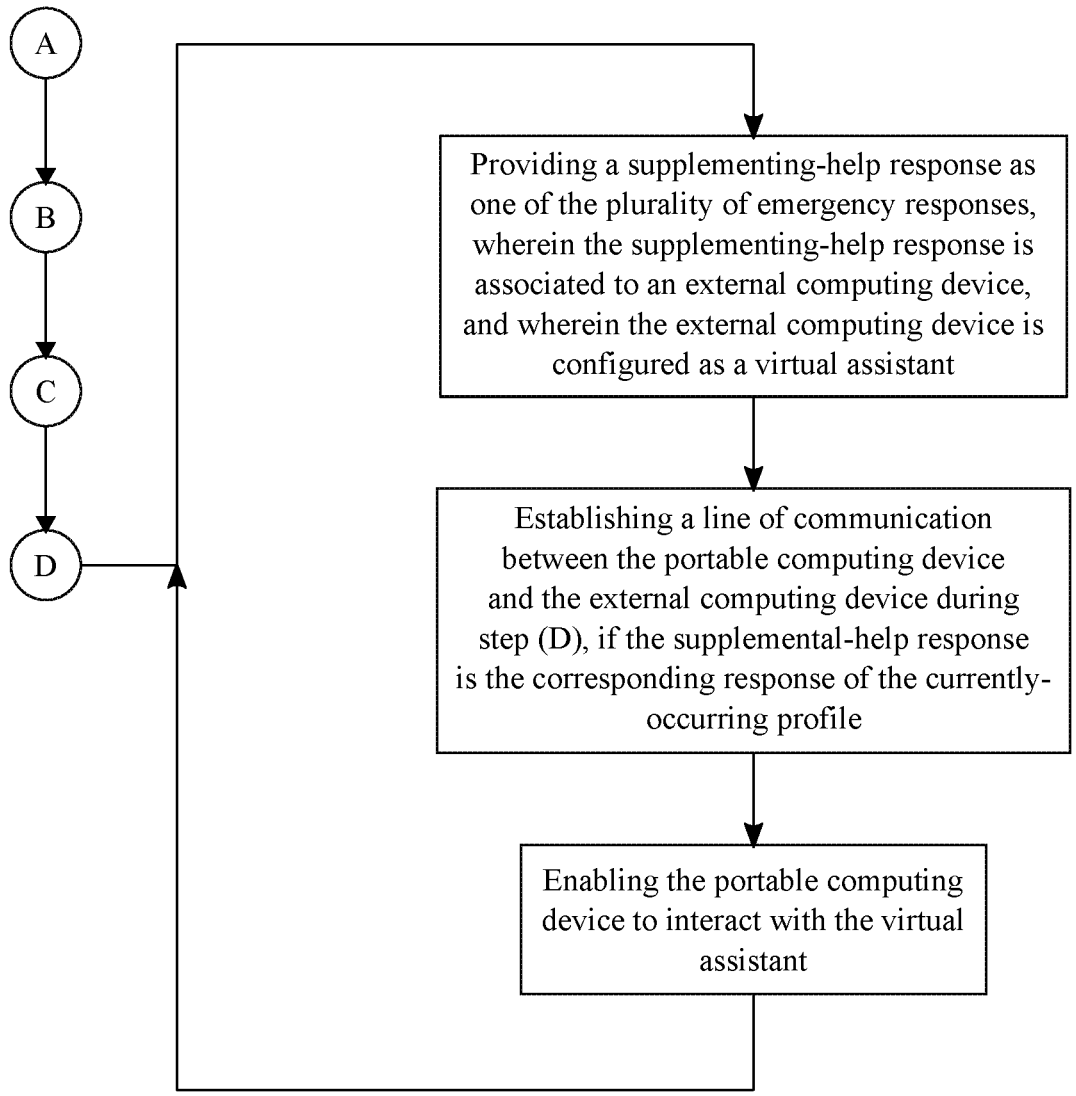
FIG. 14 is a flowchart illustrating a subprocess to execute a supplementing-help response for an emergency.

As can be seen in FIG. 14, another subprocess implements a supplementing-help response as one of the plurality of emergency responses, which requires an external computing device that is configured as a virtual assistant (e.g. Apple's Ski, Amazon's Alexa, Google's Google Assistant, etc.). The supplementing-help response allows the user to access and interface all of the features and tools that are available through the virtual assistance. The supplementing-help response can be a corresponding response for either an immediate emergency profile or a potential emergency profile. Moreover, if the supplementing-help response is the corresponding response of the currently-occurring profile, then a line of communication is established between the portable computing device and the external computing device during Step D, which allows the user to interact with the virtual assistant through the portable computing device.

Figure 15:
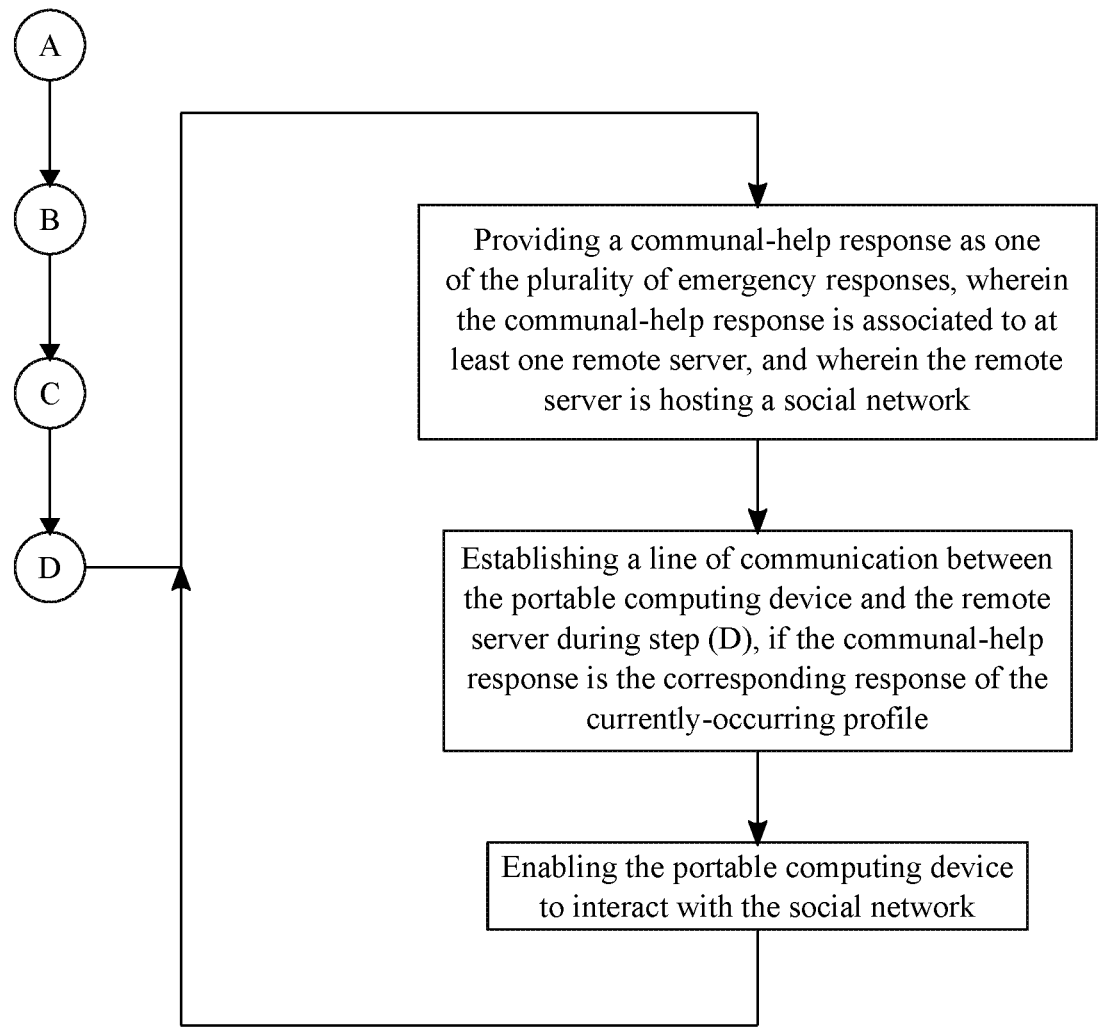
FIG. 15 is a flowchart illustrating a subprocess to execute a communal-help response for an emergency.

As can be seen in FIG. 15, another subprocess implements a communal-help response as one of the plurality of emergency responses, which requires at least one remote server that is hosting a social network (e.g. Facebook, Instagram, Twitter, etc.). The communal-help response allows the user to access and interface all of the features and contacts that are available through the social network. The communal-help response can be a corresponding response for either an immediate emergency profile or a potential emergency profile. Moreover, if the communal-help response is the corresponding response of the currently-occurring profile, then a line of communication is established between the portable computing device and the remote server during Step D, which allows the user to interact with the social network through the portable computing device. In addition, the communal-help response is very useful in emergency situation that involve a lot of people. For example, the communal-help response would be very used in a school-shooting emergency, which would allow the military, the police force, the first responders, the students, and/or the school faculty to communicate amongst each other.

Road-rage and adolescent bullying are other examples of how the communal-help response can be implemented with the present invention.

Figure 16:
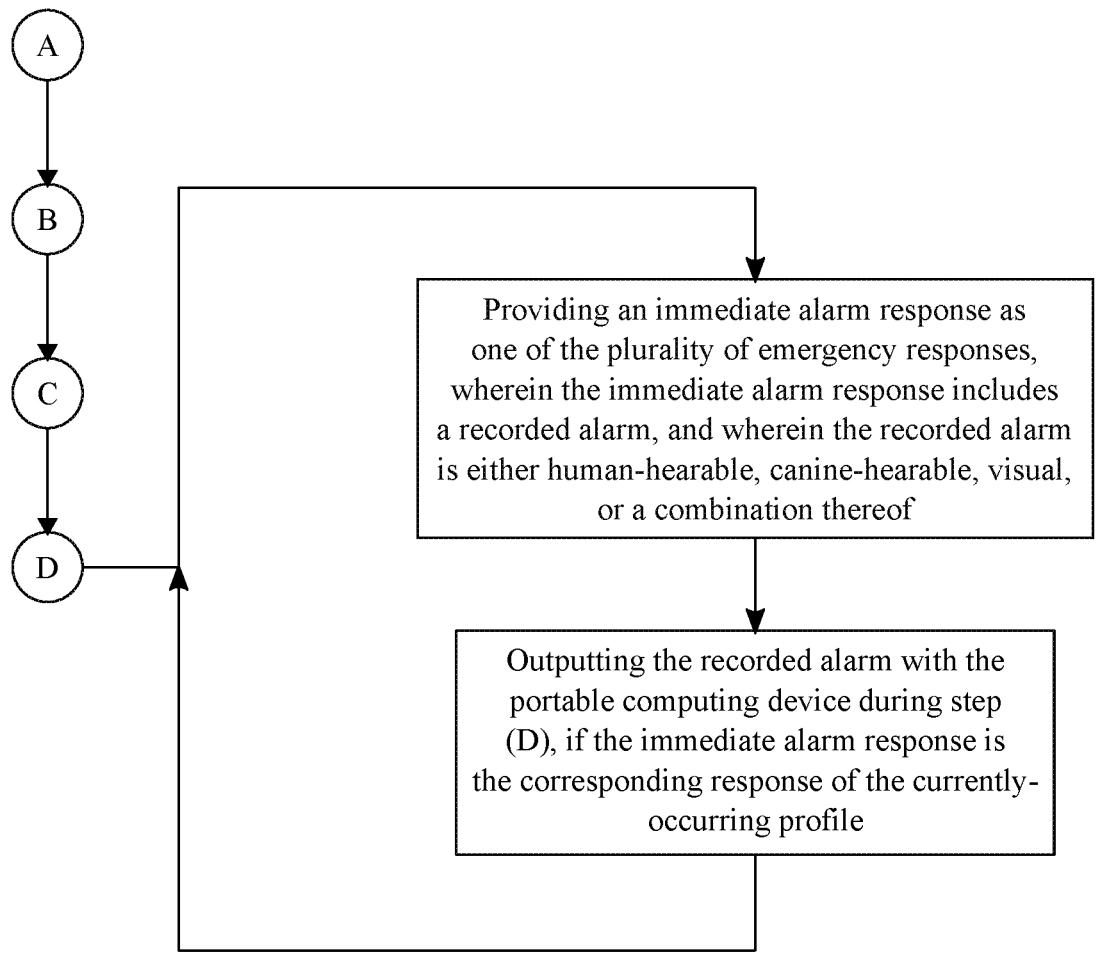
FIG. 16 is a flowchart illustrating a subprocess to execute an immediate alarm response for an emergency.

As can be seen in FIG. 16, another subprocess implements an immediate alarm response as one of the plurality of emergency responses, which requires a recorded alarm stored on the portable computing device. The recorded alarm is sound and/or visual that is used as a deterrence or an attention grabber. One example of the recorded alarm is as an ultrasonic canine whistle, which would be used to deter a canine attack. Another example of the recorded alarm is as a loud cacophony, which would be used to grab the attention of some distant bystanders that could provide assistance in case of an emergency. The recorded alarm can be, but is not limited to, human-hearable, canine-hearable, visual, or a combination thereof. Thus, if the immediate alarm response is the corresponding response of the currently-occurring profile, then the portable computing device outputs the recorded alarm during Step D.

Figure 17:
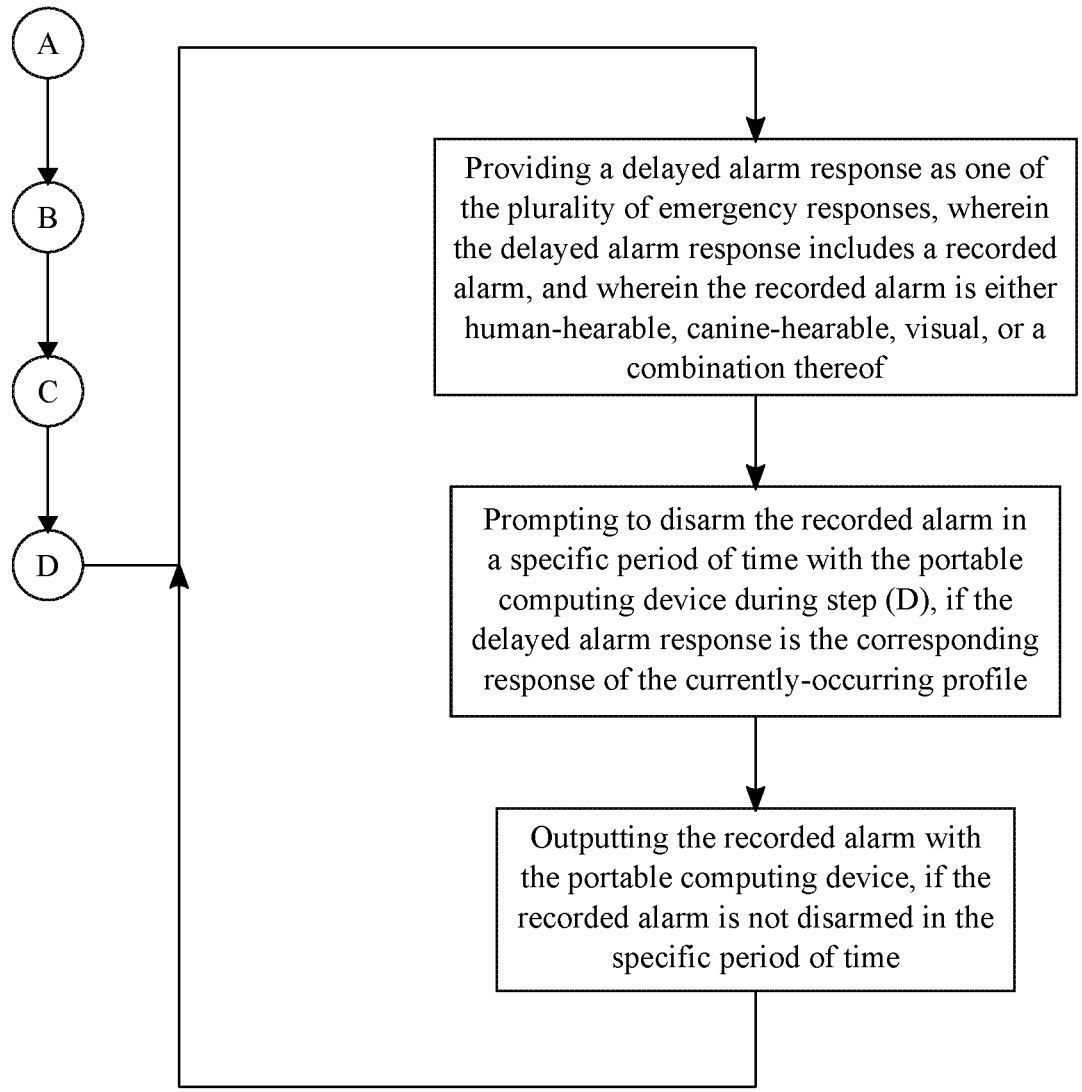
FIG. 17 is a flowchart illustrating a subprocess to execute a delayed alarm response for an emergency.

As can be seen in FIG. 17, another subprocess implements a delayed alarm response as one of the plurality of emergency responses, which similarly requires a recorded alarm stored on the portable computing device. Again, the recorded alarm is sound and/or visual that is used as a deterrence or an attention grabber, and the recorded alarm can be, but is not limited to, human-hearable, canine-hearable, visual, or a combination thereof. However, the difference between the immediate alarm response and the delayed alarm response is that the immediate alarm response is triggered through an automated process and the delayed alarm response is triggered only if the user does not disarm the delayed alarm response within a specific period of time. The delayed alarm response is used to prevent accidental activation of alarms. Thus, if the delayed alarm response is the corresponding response of the currently-occurring profile, then the portable computing device prompts to disarm the recorded alarm in a specific period of time during Step D. The specific period of time should not be too long so as to inappropriately reduce the urgency of the emergency situation that triggered the delayed alarm response. However, the portable computing device does output the recorded alarm, if the recorded alarm is not disarmed in the specific period of time.

Figure 18:
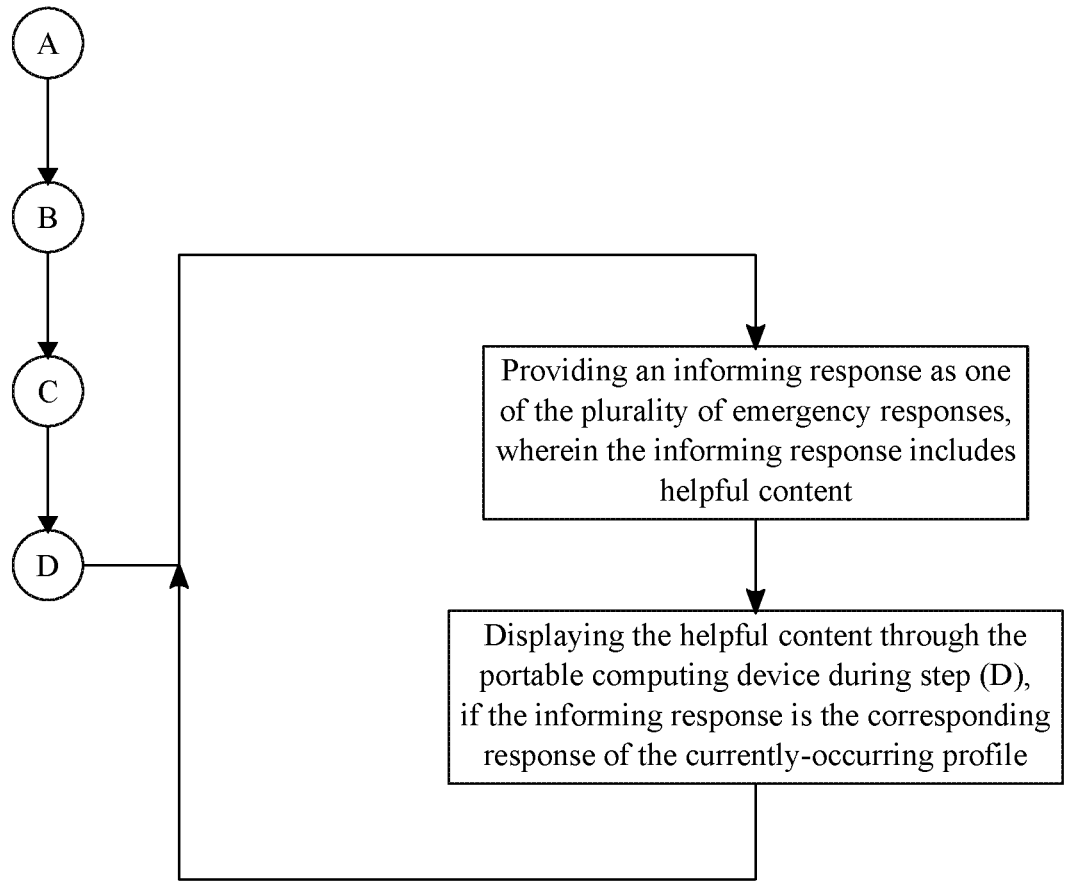
FIG. 18 is a flowchart illustrating a subprocess to execute an informing response for an emergency.

As can be seen in FIG. 18, another subprocess implements an informing response as one of the plurality of emergency responses, which requires helpful content that is related to an emergency situation. For example, if the emergency situation is a tornado warning, then the helpful content from the informing response should disclose a procedure on how to stay safe in a tornado. Thus, if the informing response is the corresponding response of the currently-occurring profile, then the helpful content is displayed through the portable computing device during Step D.

Figure 19:
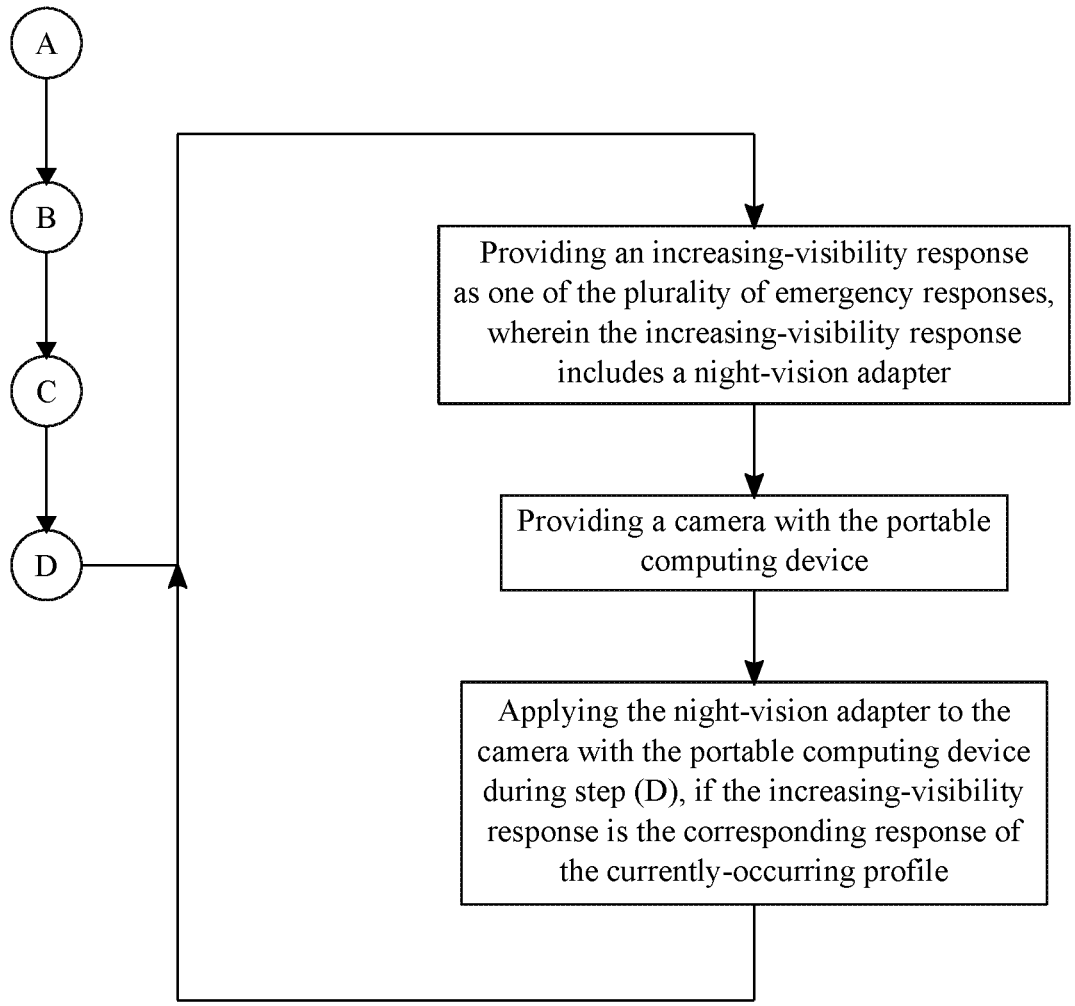
FIG. 19 is a flowchart illustrating a subprocess to execute an increasing-visibility response for an emergency.

As can be seen in FIG. 19, another subprocess implements an increasing-visibility response as one of the plurality of emergency responses, which requires a night-vision adapter. The night-vision adapter is used to improve visibility when the user is in a dangerous dark environment. Thus, if the increasing-visibility response is the corresponding response of the currently-occurring profile, then the portable computing device applies the night-vision adapter to the camera during Step D. In one embodiment of the night-vision adapter, the night-vision adapter functions by removing an infrared filter from a camera of the portable computing device, which allows the camera to capture more infrared light and consequently enables night vision for the portable computing device. In another embodiment of the night-vision adapter, the portable computing device has a set of infrared emitters that shine on the surrounding areas, which is then captured by a set of infrared detectors for the portable computing device and consequently enables night vision for the portable computing device. In some other embodiments, thermal imaging is used instead of a night-vision adapter in order to implement night vision with the present invention.

Figure 20:
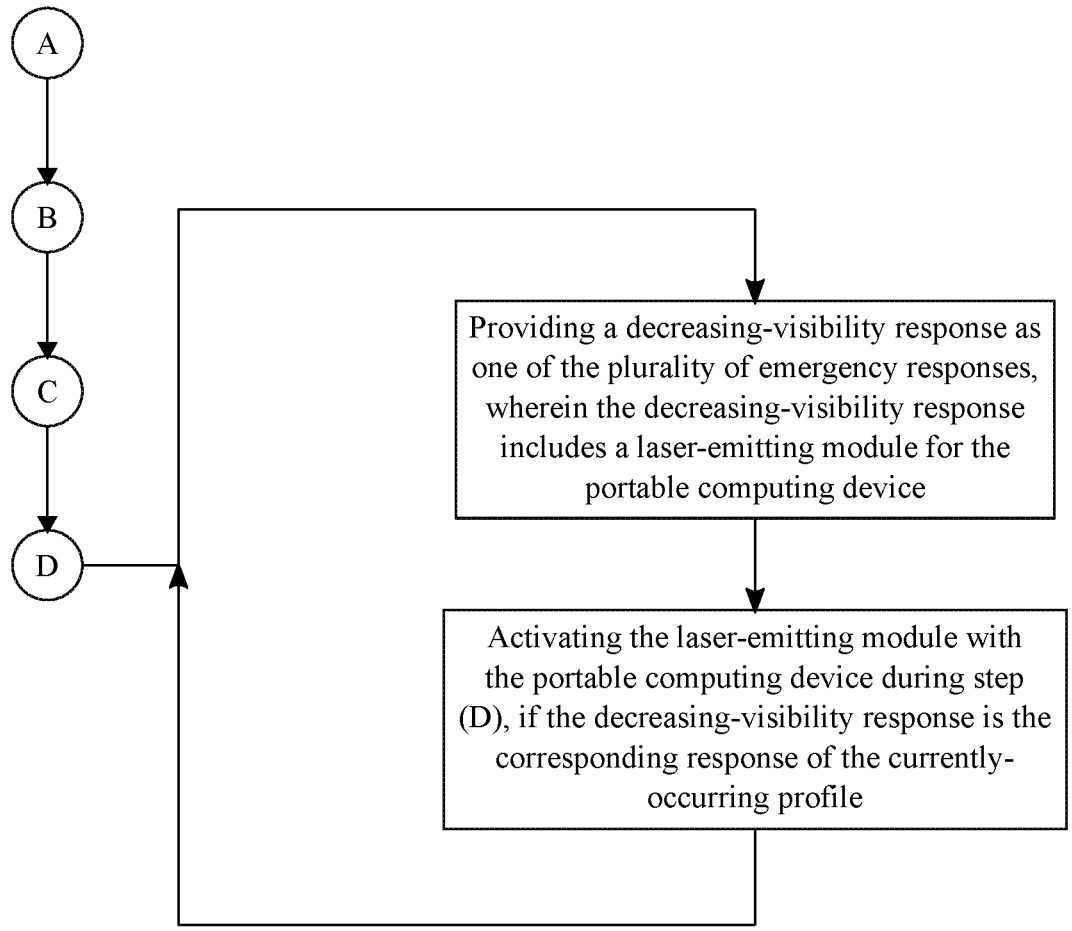
FIG. 20 is a flowchart illustrating a subprocess to execute a decreasing-visibility response for an emergency.

As can be seen in FIG. 20, another subprocess implements a decreasing-visibility response as one of the plurality of emergency responses, which requires a laser-emitting module for the portable computing device. For example, the laser-emitting module can be shined into the eyes of an attacker or an abductor in order to subdue the attacker or the abductor. Thus, if the decreasing-visibility response is the corresponding response of the currently-occurring profile, then the portable computing device activates the laser-emitting device during Step D.

In some embodiments of the present invention, the user can enter a command into the portable computing device that is able to put the present invention into a defender mode. The defender mode keeps the present invention running on the background for the portable computing device so that any feature of the present invention is readily available to the user. Conversely, the user can enter a command into the portable computing device that is able to put the present invention into a safe mode. The safe mode keeps the present invention offline so that all features are not available to the user.

In some embodiments of the present invention, the portable computing device is configured with a wristband that is tamper resistant. One way that the wristband is tamper resistant is that the wristband is made of extra strong fibers. Another way that the wristband is tamper resistant is that the latching mechanism for the wristband is resistant to cutting or being ripped off. Moreover, the wristband may be configured with a fingerprint reading pad that is inconspicuously located on the inner surface. The portable computing device may be programmed to activate some automated features of the present invention, if the wristband is separated from the user against their will. The portable computing device may also be programmed to be activate safe mode when the fingerprint reading pad is touched twice in sequence or touched in some other specified pattern. Furthermore, the portable computing device may be programmed to be activate defender mode when the fingerprint reading pad is touched once or touched in some other specified pattern Although the invention has been explained in relation to its preferred embodiment, it is to be understood that many other possible modifications and variations can be made without departing from the spirit and scope of the invention as hereinafter claimed.

Supplemental Description

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of personal security, and systems and devices to facilitate personal security, embodiments of the present disclosure are not limited to use only in this context.

Figure 21:
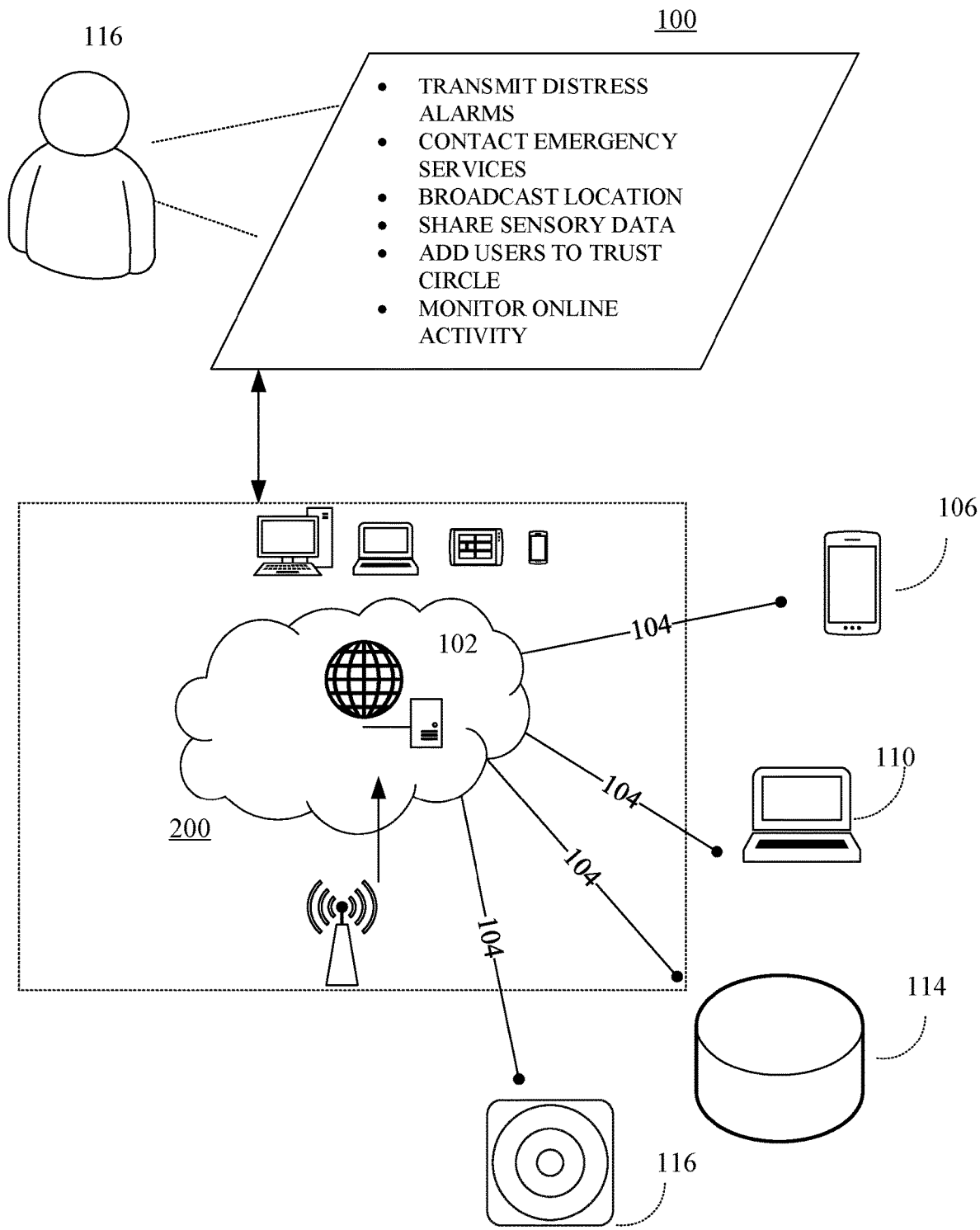
FIG. 21 is an illustration of an online platform 100 consistent with various embodiments of the present disclosure.

FIG. 21 is an illustration of an online platform 100 consistent with various embodiments of the present disclosure. By way of non-limiting example, the online platform 100 for facilitating personal security may be hosted on a centralized server 102, such as, for example, a cloud computing service. The centralized server 102 may communicate with other network entities, such as, for example, a mobile device 106 (such as a smartphone, a laptop, a tablet computer etc.), other electronic devices 110 (such as desktop computers, server computers etc.), databases 114 and sensors 116 (e.g. sound sensor, image sensor, temperature sensor, pressure sensor, motion sensor, physiological sensors, etc.) over a communication network 104, such as, but not limited to, the Internet. Further, users of the platform may include relevant parties such as, but not limited to children, parents, doctors, soldiers, police officers, and other individuals. Accordingly, in some instances, electronic devices operated by the one or more relevant parties may be in communication with the platform.

A user 112, such as the one or more relevant parties, may access online platform 100 through a web based software application or browser. The web based software application may be embodied as, for example, but not be limited to, a website, a web application, a desktop application, and a mobile application compatible with a computing device 200.

According to some embodiments, the online platform may be configured to communicate with a personal security device to facilitate personal safety and security for users. The personal security device may allow users to contact emergency services, emergency contacts set by the user, and to set off a distress alarm in situations of emergency. The personal security device may be a wearable computer, such as but not limited to a smartwatch, smart glass, or interactive fabric/accessory (e.g. hat, cap, shoes, shirt, pants etc. embedded with computing devices), or a mobile device such as, but not limited to a smartphone, or a computer tablet and so on. The personal security device may include a communication device configured to communicate over a communication network such as, but not limited to, a cellular network, a satellite network, a personal area network, Bluetooth, Zig-Bee, Internet and so on. The personal security device may also include one or more sensors such as, but not limited to, an image sensor, a microphone, a location sensor (e.g. GPS receiver), an accelerometer, a gyroscope, an electronic compass, etc. The sensors may be used to receive information from the environment of the user. Further, the personal security device may also include sensors to monitor the health of the users. Health monitoring sensors may include, but may not be limited to temperature sensor, heart rate sensor, or a blood pressure sensor. Further, the personal security device may also include a processor. The processor may be used to process the inputs received from the one or more sensors of the personal security device. Accordingly, the personal security device may receive inputs from the environment of the user and may determine when a threat is present. A threat may be defined as a possibility of pain, injury, damage, or other hostile action to the user from any source. The threat may be determined to be present by the personal security device through means such as voice recognition of keywords like "help" or other keywords. Further, the user may also program additional keywords in the personal security device by recording some voice samples in the personal security device. The processor may recognize the voice of the user and determine threat based on the voice sample, the spoken keyword, and the tone of the voice. Further, the processor may also analyze and recognize other distress parameters such as increased or decreased heart rate, or blood pressure. Upon detection of a threat, the personal security device or the smart device may launch an audio or video call to one or more emergency contacts set by the user or to emergency services like 911 over a communication network like a mobile network or the Internet. Alternatively, the user may choose to call pre-set emergency contacts or to emergency services like 911 manually upon detection of a threat.

For example, the personal security device may also include fall detection. The processor may receive inputs from the gyroscope and may recognize if the personal security device and therefore the user may be falling or may be thrown about in different directions. The personal security device may then engage the emergency features and make a 911 call and or alert the emergency contacts decided by the user. The personal security device may also broadcast the location of the user to all emergency contacts and emergency services. Further, the personal security device may contain a health alert feature that may detect the heart rate, and blood pressure, of the user and may engage the emergency features of the personal security device if the personal security device detects senses an extreme rise or fall in the user's heart rate.

Further, the personal security device may also help in deterring attacks on the user by other individuals. The user may program keywords and/or voice tones to initiate the security features of the personal security device. For example, if the user is being attacked or abducted by adult perpetrators, the user may be overtaken before being able to manually trigger the emergency features of the personal security device. Therefore, the emergency services may be activated by voice recognition or through sensory data like the readings in the gyroscope that may indicate that the user may be have been forcefully taken into custody, or the heart rate sensor, that may indicate a sudden rise in the heart rate of the user. The emergency features of the personal security device may include emission of a high decibel alarm or siren that may be heard from large distance and initiation of an emergency call to emergency contacts of the user or to the emergency services like 911. Further, the personal security device may also engage location or GPS feature to be able to transmit locations of the user to emergency contacts and relevant authorities.

In further embodiments, the personal security device may also deter attacks on the user from vicious animals like stray dogs. The user may program the personal security device with the sounds and tones of aggressive animals to recognize the sounds and tones and engage the emergency features of the personal security device. Further, the online platform 100 may gather a database of common sounds made by vicious animals from various users. The online platform 100 may, therefore, allow the personal security devices to recognize distress sounds like a dog or animal attack even if they may not have been programmed by the user. The emergency features may include emission of high or low-frequency sounds that may deter the attacking animal. Further, the personal security device may rotate between the emission of a human alarm and the animal attack emission sound. The human alarm may alert other nearby people that the user may be in trouble and may also augment the animal attack emission sound in deterring the animal attack. Further, in addition to utilizing ultrasonic frequency to deter animal aggression and attacks, the personal security device may also include other sounds found to be effective in controlling animal aggression. The sounds may be recorded and embedded in the personal security device and may be launched automatically upon command or recognition of animal aggression. Such sounds may include, but may not be limited to, the sound of a tin can filled with marbles and vigorously shaken. Further, the personal security device may also include a laser light. The laser light may light up along with the audible alarm for both human and animal attacks. The laser light may be pointed at the attacker's eyes making it hard the attacker to see the user.

In further embodiments, the personal security device may also contain a trip timer function. The trip timer function may allow the user to set a time within which the user may have to turn the trip timer off manually. If the user does not or cannot turn the trip timer off, an alarm may sound after the trip timer elapses. The personal security device may also send a notification to specified contacts and the emergency services along with the GPS location of the user.

In further embodiments, where the personal security device may be a wearable computer, the personal security device may also include additional fastening mechanisms to securely fasten the personal security device to the user. For example, if the personal security device is a smartwatch, the personal security device may include interchangeable watch straps, that may also be wear and tear resistant, waterproof, and may include a stronger weave and a more secure fastening mechanism so that the personal security device may be more resistant to forced removal. Further, the personal security device may engage the emergency features if the personal security device is forcefully being pulled off the user. Further, the wearable device, such as a smart watch band may include a proprietary fingerprint recognition pad located in an inconspicuous location. Accordingly, when a user is commanded to take the wearable device off, the user could place a finger over the fingerprint recognition pad while taking the wearable device off which may launch a security feature. In an instance, the security feature may be programmable by the user to include or exclude an audible alarm function. Further, the wearable device may also include a retinal scan feature for activation when programmed to use this feature.

In further embodiments, the personal security device may also launch the camera and the microphone while making an emergency call to an emergency contact selected by the user or to the emergency services like 911. Therefore, the emergency contact or the 911 dispatcher may be able to see and hear the user from the camera of the personal security device. The dispatcher may further contact the required department like the police department, Fire, EMS or other such first responders. Further, the emergency responders may also possess a personal security device, and may, therefore, be able to view the user in distress. Therefore, a chain of communication may be created between the user and the emergency responders. Further, if the user has a medical emergency, the EMS may notify a nearby hospital of the medical situation of the user. Further, the hospital may also possess a personal safety device or personal safety app and may be able to view the user and prepare for any necessary treatment ahead of time in a better manner. Further, in a situation where the user may not be in a position to be treated by emergency responders, appropriate parties like a trained doctor may be able to assist user remotely and guide the emergency responders in identifying an area of concern that may need to be addressed.

In further embodiments, the personal security device may operate on multiple levels of threat detection. The levels of threat detection may begin from a basic level for instance level 1, where a few sensors may receive inputs to detect threats in the environment of a user. If the sensors active in level 1 detect a threat, the next level of threat detection may be activated, where a further number of sensors may be activated to further detect the level of threats. The levels may be customizable by the user, wherein the user may select the sensors and inputs that the personal security device may analyze to detect threats. For example, the in level 1, only the microphone may receive inputs from the environment of the user. If the microphone receives sound input that may be characteristic of a threat, further sensors, like the camera may begin operating. The camera may then take pictures, and the device may perform image recognition to recognize if a threat may be present. For example, if the microphone detects a barking dog, the camera may be activated in level 2 wherein the camera of the personal security device may be activated, that may recognize objects near the user to detect whether a dog may be present. Further, the personal security device may also include a multistep process to initialize the security features of the personal security device. Different commands may set the commands to different modes wherein the personal security device may work in different ways. For instance, if the user chooses the "launch defender" mode, the personal security device may be in a state of hibernation until a threat is manually selected by the user. Further, a separate command, like the "launch emergency mode" command may initialize all security features of the personal security application wherein all the sensors may be active and receiving constant inputs to determine a threat.

In further embodiments, the personal security device may also have military applications. Multiple military personnel, including soldiers, officers, and the personnel in military bases may be equipped with personal security devices. The personal security devices may be wearable devices like smart glasses, smart watches, or even smart fabrics. The personal security device of a soldier may receive inputs from sensors like camera, microphone, gyroscope, accelerometer, compass, etc. and transmit this data over a communication network to the online platform 100. Therefore, personal security devices of all the soldiers that may be in a unit or a battalion may be interconnected in such a manner that the soldiers and other military personnel may be constantly able to monitor an active situation through the point of view of any soldier through the corresponding personal security device. Therefore, the soldiers may be able to come up with a better strategy to combat an active situation. Further, personal security device of a soldier may also broadcast distress signals upon detection of a threat. The personal security device may detect a situation of threat from various inputs received from sensors and may contact emergency services. Further, medical personnel may be able to view the active situation through a personal security device and may be able to assist the soldier in need.

In further embodiments, the personal security device may also have applications for hunters and fishermen. A hunter or fisherman may be equipped with a personal security device. The personal security device may constantly monitor the level of threat for the hunter or fisherman through sensors. Further, the personal security device may be connected to personal security devices of other hunters or fishermen in the region through the communication device over a communication network. Therefore, the hunters or fishermen may be able to devise a better strategy to catch the respective prey.

In further embodiments, the personal security device may also have applications for business establishments. A business establishment may facilitate the employees with personal security devices. The personal security devices may be wearable computers, mobile devices, or even desktop systems. The personal security device may make use of the camera, and microphone, display, and other sensors, and may make use of communication device to contact another personal security device as if in a conference. The users may be able to make voice, or video calls manually, or through voice commands.

In further embodiments, the personal security device may also include support for third-party voice recognition software, voice-controlled smart speakers like the Amazon Echo® and intelligent personal assistants like Amazon Alexa®. The personal security device may be able to connect to third-party applications like the Alexa® app and to voice-operated speakers such as the Amazon Echo® or the Amazon Echo Dot® over communication networks such as but not limited to the internet, Wi-Fi, and Bluetooth. Therefore, thee user may use voice commands for the third-party products like the voice-controlled smart speaker to inquire about a personal security device of a user. For instance, the user may inquire about the location or the health of a user or users such as children or elderly parents The smart speaker, through the third party application, may communicate with the personal security device of the user. Further, the personal security device, upon receiving a notification about the inquiry from the smart speaker may transmit the data collected from the one or more sensors. For example, a user (User 1) may inquire about the location and the heart rate of another user (User 2) through the smart speaker. The personal security device of User 2 may transmit the location, and the heart rate over the communication network and the smart speaker may broadcast the received information to User 1. Further, if the personal security device of a User 2 detects a threat, the personal security device may send a notification about the threat, and the location of User 2 to the connected smart speaker that may broadcast the received information to User 1. Further, a single smart speaker system may be connected to multiple personal security devices of multiple users. The multiple personal security devices may also transmit back specific information when inquired through the smart speaker, and may transmit a detected threat.

In further embodiments, the personal security device may also include an anti-road rage feature. The user may select the anti-road rage feature with a command such as "No Rage" or "launch No Rage" for example, if the user may be feeling threatened by another vehicle while driving. The personal security device may constantly broadcast the location of the user to emergency services, and emergency contacts, and may begin recording audio and video so that the vehicle, vehicle number, and the perpetrator driving the vehicle may be recorded.

In further embodiments, the personal security device may also include an anti-bullying feature. The personal security device may receive inputs from sensors like microphones, and cameras, and process the received information to ascertain whether the inputs received may be considered as bullying of the user. For example, the personal security device may recognize threatening words, or phrases, that may have been said against the user. The personal security device may further analyze the impact of such inputs on the user's health. For example, whether after hearing threatening words from external sources, there is a change in the heart rate and breathing patterns of the user. Further, the personal security device may be connected to external social media accounts of the user through the online platform 100.

The online platform 100 may thus recognize any messages or comments received by the user on any social media accounts that may be classified as cyberbullying. Further, the personal security device may collect, and save all instances of inputs received that may be classified as bullying and may present the inputs as evidence to the emergency contacts, or concerned authorities. Further, the evidence saved by the personal security device may be used for threats, slander and libel suits.

In further embodiments, the personal security device may also receive information like restraining orders that the user may have against other individuals, or from other individuals, parole information, and any other legal information, through the online platform 100. The online platform 100 may be connected to databases like legal databases, and may access information like reports of restraining orders, bail, and parole information of individuals. Further, the personal security may receive information from sensor, for example, the camera of the personal device may constantly monitor individuals in the vicinity of the user, and pay process the recorded images to identify whether any individual may be a threat to the user. The individual may have violated legal restraining orders, or even parole. Further, the personal security device may alert the concerned authorities, emergency contacts, or even the user if a threat may have been detected.

In further embodiments, the personal security device may also monitor the user's online activity through the online platform 100. The online platform may track the cookies from the website that the user may visit, and may detect whether a website that the user may be visiting be harmful. Further, the user may also select websites by category that the user may not want to visit. For instance, if the user selects that the user may not be able to view social media websites, the personal security device may alert the user every time the user may accidentally open a social media website. Further, the online activity of the user may also be monitors through connected personal security devices of the parents of the user. The personal security device of the user may constantly send browsing data to the parent's personal security device. Further, the personal security device of the user may also send an alert to the personal security device of the parent if the user tries to view a website that may be blocked. Further, the browsing time of the user may also be monitored, and limited.

In further embodiments, the personal security device may also include self-defense and personal security tips and illustrations. The personal security tips and illustrations may be pre-loaded in the personal security device and may be viewed by the user at any time. Further, the user may also be able to view the personal security tips and illustrations in a larger form with the personal security tips and illustrations projected onto an external screen, or surface, other than the personal security device itself.

In further embodiments, the online platform 100 may allow multiple users with personal security devices to build a trust circle. A trust-circle may be a collection of users who may add each other to the trust-circle and may receive notifications about other users in the trust circle. A user may send a request to another user with a personal security device to be added the user's trust circle. The second user may choose to accept or ignore the request. Further, when a user may be in a threatening situation, the personal security device may notify all other users in the user's trust circle and may broadcast information like the GPS location, and the live images and audio from the camera and microphone of the personal security device. Therefore, the personal security device may make use of crowdsourcing to respond to a threat to a user in a situation where the emergency services and the first responders may not be able to reach in time, especially in conditions with users in the military. For example, if a user has a heart attack, the personal security device may contact the emergency services like 911 and also send a notification to all users in the user's trust circle. If the emergency services may not be able to reach the user on time, but another user in the user's trust circle may be able to reach the user in a lesser amount of time, the user may be saved by receiving proper medical attention or first aid in time.

Further, in some embodiments, the system may further include one or more display devices pre-loaded with the personal safety app. Further, the one or more display devices may be in communication with the online platform. Accordingly, data collected from a plurality of personal safety devices may be transmitted to the one or more display devices which may be located, for example, in 911 call centers, first responder dispatch centers, military bases, business offices etc. As a result, in an instance, information such as images and corresponding user data may be presented on a larger screen for convenient viewing.

Figure 22:
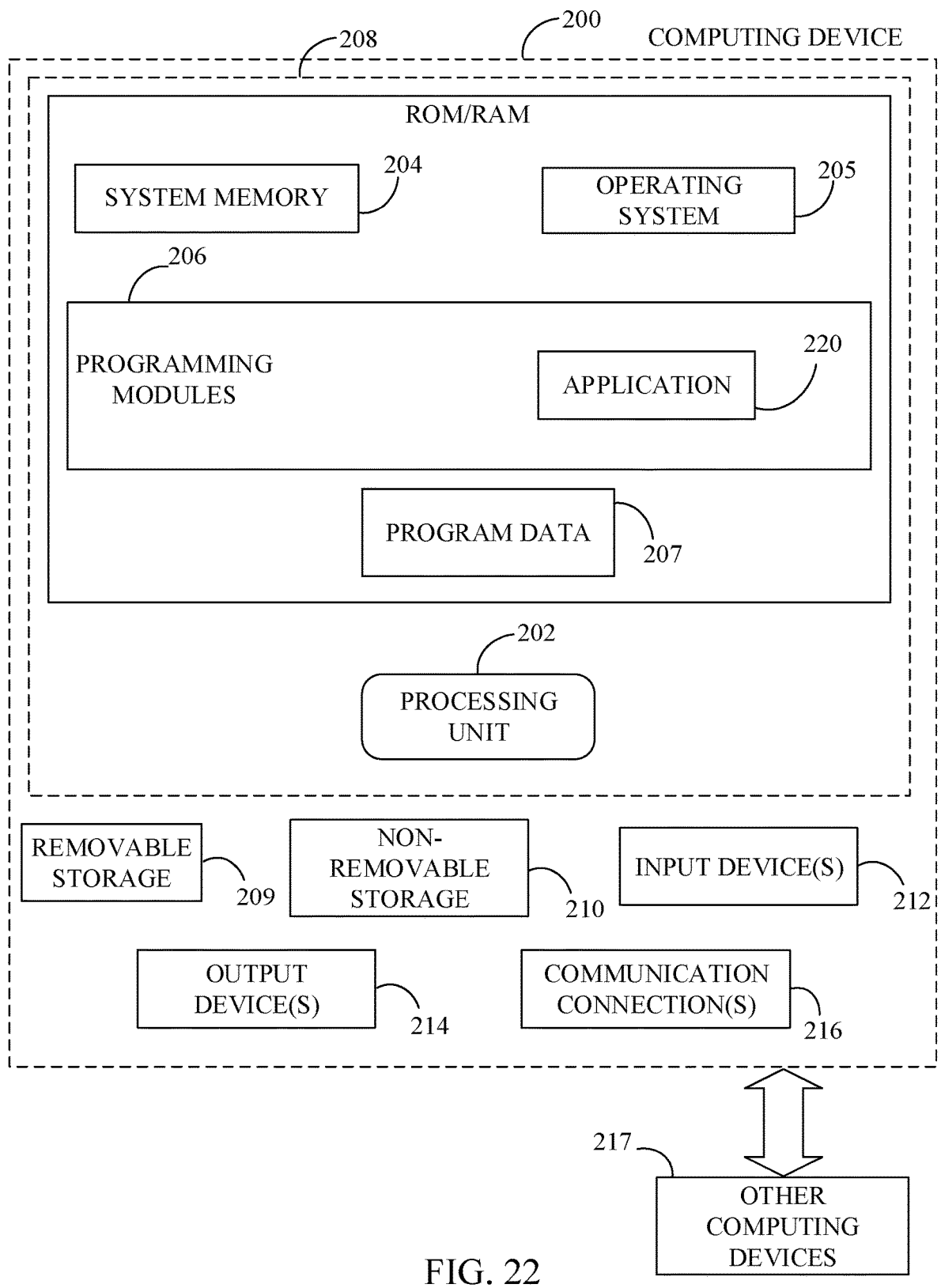
FIG. 22 is a block diagram of a computing device for implementing the methods disclosed herein, in accordance with some embodiments.

With reference to FIG. 22, a system consistent with an embodiment of the disclosure may include a computing device or cloud service, such as computing device 200. In a basic configuration, computing device 200 may include at least one processing unit 202 and a system memory 204. Depending on the configuration and type of computing device, system memory 204 may comprise, but is not limited to, volatile (e.g. random-access memory (RAM)), non-volatile (e.g. read-only memory (ROM)), flash memory, or any combination. System memory 204 may include operating system 205, one or more programming modules 206, and may include a program data 207. Operating system 205, for example, may be suitable for controlling computing device 200's operation. In one embodiment, programming modules 206 may include image-processing module, sound processing module, speech recognition module, machine learning module and/or image classifying module. Furthermore, embodiments of the disclosure may be practiced in conjunction with a graphics library, other operating systems, or any other application program and is not limited to any particular application or system. This basic configuration is illustrated in FIG. 22 by those components within a dashed line 208. Computing device 200 may have additional features or functionality. For example, computing device 200 may also include additional data storage devices (removable and/or non-removable) such as, for example, magnetic disks, optical disks, or tape. Such additional storage is illustrated in FIG. 22 by a removable storage 209 and a non-removable storage 210. Computer storage media may include volatile and nonvolatile, removable and non-removable media implemented in any method or technology for storage of information, such as computer-readable instructions, data structures, program modules, or other data. System memory 204, removable storage 209, and non-removable storage 210 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 200. Any such computer storage media may be part of device 200. Computing device 200 may also have input device(s) 212 such as a keyboard, a mouse, a pen, a sound input device, a touch input device, a location sensor, a camera, a biometric sensor, etc. Output device(s) 214 such as a display, speakers, a printer, etc. may also be included. The aforementioned devices are examples and others may be used.

Computing device 200 may also contain a communication connection 216 that may allow device 200 to communicate with other computing devices 218, such as over a network in a distributed computing environment, for example, an intranet or the Internet.

Communication connection 216 is one example of communication media.

Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 204, including operating system 205. While executing on processing unit 202, programming modules 206 (e.g., application 220 such as a media player) may perform processes including, for example, one or more stages of methods, algorithms, systems, applications, servers, databases as described above. The aforementioned process is an example, and processing unit 202 may perform other processes. Other programming modules that may be used in accordance with embodiments of the present disclosure may include sound encoding/decoding applications, machine learning application, acoustic classifiers etc.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

What is claimed is:

1. A method of managing personal security, the method comprises the steps of:
   (A) providing a plurality of emergency profiles managed by a portable computing device, and providing an immediate emergency profile as one of the plurality of emergency profiles, wherein the immediate emergency profile includes a plurality of physical trauma cues respectively corresponding to external forces applied on a user of the portable computer and wherein the portable computing device includes at least one inertial sensor;
   (B) providing a plurality of emergency responses managed by the portable computing device, wherein each emergency profile is associated with at least one corresponding response from the plurality of emergency responses, and providing an immediate alarm response as one of the plurality of emergency responses, wherein the immediate alarm response includes a recorded alarm, and wherein the recorded alarm is either human-hearable, canine-hearable, visual, or a combination thereof;
   (C) identifying at least one currently-occurring profile with the portable computing device, wherein the currently-occurring profile is any profile from the plurality of emergency profiles, prompting to activate the immediate emergency profile with the portable computing device, and designating the currently-occurring profile as the immediate emergency profile with the portable computing device, if the immediate emergency profile is selectively activated through the portable computing device, and receiving inertial input data through the inertial sensor, and comparing the inertial input data to each physical trauma cue with the portable computing device in order to distinguish physical trauma ques from normal external forces applied to the user by identifying a matching cue from the plurality of physical trauma cues, and designating the currently-occurring profile as the immediate emergency profile with the portable computing device, if the matching cue is identified from the plurality of physical trauma cues; and
   (D) executing the corresponding response of the currently-occurring profile with the portable computing device, and outputting the recorded alarm with the portable computing device, if the immediate alarm response is the corresponding response of the currently-occurring profile.

2. The method of managing personal security, the method as claimed in claim 1 comprises the steps of:
   providing an immediate emergency profile as one of the plurality of emergency profiles, wherein the immediate emergency profile includes a plurality of spoken distress cues;
   providing a microphone with the portable computing device;
   receiving audible input data through the microphone;
   comparing the audible input data to each spoken distress cue with the portable computing device in order to identify a matching cue from the plurality of spoken distress cues; and
   designating the currently-occurring profile as the immediate emergency profile with the portable computing device during step (C), if the matching cue is identified from the plurality of spoken distress cues.

3. The method of managing personal security, the method as claimed in claim 1 comprises the steps of:
   providing an immediate emergency profile as one of the plurality of emergency profiles, wherein the immediate emergency profile includes a plurality of audible danger cues;
   providing a microphone with the portable computing device;
   receiving audible input data through the microphone;
   comparing the audible input data to each audible danger cue with the portable computing device in order to identify a matching cue from the plurality of audible danger cues; and
   designating the currently-occurring profile as the immediate emergency profile with the portable computing device during step (C), if the matching cue is identified from the plurality of audible danger cues.

4. The method of managing personal security, the method as claimed in claim 1 comprises the steps of:
   providing an immediate emergency profile as one of the plurality of emergency profiles, wherein the immediate emergency profile includes a plurality of medical distress cues;
   providing at least one biometric sensor with the portable computing device;
   receiving biometric input data through the biometric sensor;
   comparing the biometric input data to each medical distress cue with the portable computing device in order to identify a matching cue from the plurality of medical distress cues; and
   designating the currently-occurring profile as the immediate emergency profile with the portable computing device during step (C), if the matching cue is identified from the plurality of medical distress cues.

5. The method of managing personal security, the method as claimed in claim 1 comprises the steps of:
   providing a potential emergency profile as one of the plurality of emergency profiles, wherein the potential emergency profile includes a minimum brightness threshold;
   providing at least one luminosity sensor with the portable computing device;
   receiving luminosity input data through the luminosity sensor; and
   designating the currently-occurring profile as the potential emergency profile with the portable computing device during step (C), if the luminosity input data is less than the minimum brightness threshold.

6. The method of managing personal security, the method as claimed in claim 1 comprises the steps of:
   providing a contacting-help response as one of the plurality of emergency responses, wherein the contacting-help response includes at least one emergency-contact information; and
   establishing a line of communication between the portable computing device and the emergency-contact information during step (D), if the contacting-help response is the corresponding response of the currently-occurring profile.

7. The method of managing personal security, the method as claimed in claim 6 comprises the steps of:
   providing a microphone with the portable computing device;
   retrieving an audio feed with the microphone; and
   relaying the audio feed through the line of communication between the portable computing device and the emergency-contact information.

8. The method of managing personal security, the method as claimed in claim 6 comprises the steps of:
providing a camera with the portable computing device;
capturing a video feed with the camera; and
relaying the video feed through the line of communication between the portable computing device and the emergency-contact information.

9. The method of managing personal security, the method as claimed in claim 6 comprises the steps of:
providing a global positioning system (GPS) module with the portable computing device;
retrieving a current geospatial location with the GPS module; and
relaying the current geospatial location through the line of communication between the portable computing device and the emergency-contact information.

10. The method of managing personal security, the method as claimed in claim 6 comprises the steps of:
prompting to enter a new emergency-contact information through the portable computing device; and
appending the new emergency-contact information into the at least one emergency-contact information with the portable computing device.

11. The method of managing personal security, the method as claimed in claim 1 comprises the steps of:
providing a supplementing-help response as one of the plurality of emergency responses, wherein the supplementing-help response is associated to an external computing device, and wherein the external computing device is configured as a virtual assistant;
establishing a line of communication between the portable computing device and the external computing device during step (D), if the supplemental-help response is the corresponding response of the currently-occurring profile; and
enabling the portable computing device to interact with the virtual assistant.

12. The method of managing personal security, the method as claimed in claim 1 comprises the steps of:
providing a communal-help response as one of the plurality of emergency responses, wherein the communal-help response is associated to at least one remote server, and wherein the remote server is hosting a social network;
establishing a line of communication between the portable computing device and the remote server during step (D), if the communal-help response is the corresponding response of the currently-occurring profile; and
enabling the portable computing device to interact with the social network.

13. The method of managing personal security, the method as claimed in claim 1 comprises the steps of:
providing a delayed alarm response as one of the plurality of emergency responses, wherein the delayed alarm response includes a recorded alarm, and wherein the recorded alarm is either human-hearable, canine-hearable, visual, or a combination thereof;
prompting to disarm the recorded alarm in a specific period of time with the portable computing device during step (D), if the delayed alarm response is the corresponding response of the currently-occurring profile; and
outputting the recorded alarm with the portable computing device, if the recorded alarm is not disarmed in the specific period of time.

14. The method of managing personal security, the method as claimed in claim 1 comprises the steps of:
providing an informing response as one of the plurality of emergency responses, wherein the informing response includes helpful content; and
displaying the helpful content through the portable computing device during step (D), if the informing response is the corresponding response of the currently-occurring profile.

15. The method of managing personal security, the method as claimed in claim 1 comprises the steps of:
providing an increasing-visibility response as one of the plurality of emergency responses, wherein the increasing-visibility response includes a night-vision adapter;
providing a camera with the portable computing device; and
applying the night-vision adapter to the camera with the portable computing device during step (D), if the increasing-visibility response is the corresponding response of the currently-occurring profile.

16. The method of managing personal security, the method as claimed in claim 1 comprises the steps of:
providing a decreasing-visibility response as one of the plurality of emergency responses, wherein the decreasing-visibility response includes a laser-emitting module for the portable computing device; and
activating the laser-emitting module with the portable computing device during step (D), if the decreasing-visibility response is the corresponding response of the currently-occurring profile.

17. The method of managing personal security, the method as claimed in claim 1, wherein the portable computing device is configured with a user restraint.

* * * * *